(12) United States Patent
Manabe et al.

(10) Patent No.: US 7,732,021 B2
(45) Date of Patent: *Jun. 8, 2010

(54) LIQUID CRYSTALLINE MEDIUM

(75) Inventors: Atsutaka Manabe, Bensheim (DE); Elvira Montenegro, Weinheim (DE); Detlef Pauluth, Ober-Ramstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 12 days.

This patent is subject to a terminal disclaimer.

(21) Appl. No.: 11/629,631

(22) PCT Filed: Jun. 8, 2005

(86) PCT No.: PCT/EP2005/006138

§ 371 (c)(1), (2), (4) Date: Jan. 16, 2008

(87) PCT Pub. No.: WO2005/123878

PCT Pub. Date: Dec. 29, 2005

(65) Prior Publication Data

US 2008/0277623 A1    Nov. 13, 2008

(30) Foreign Application Priority Data

Jun. 18, 2004   (DE)   ................ 10 2004 029 492

(51) Int. Cl.
  *C09K 19/30* (2006.01)
  *C09K 19/12* (2006.01)
  *C09K 19/20* (2006.01)

(52) U.S. Cl. .............. 428/1.1; 252/299.63; 252/299.66; 252/299.67

(58) Field of Classification Search .................. 428/1.1; 252/299.63, 299.66, 299.67
See application file for complete search history.

(56) References Cited

U.S. PATENT DOCUMENTS

| | | | |
|---|---|---|---|
| 6,210,603 B1 * | 4/2001 | Kondo et al. ........... 252/299.66 |
| 6,565,933 B2 * | 5/2003 | Tarumi et al. ................ 428/1.1 |
| 6,596,350 B2 * | 7/2003 | Tarumi et al. ................ 428/1.1 |
| 6,669,998 B2 * | 12/2003 | Tarumi et al. ................ 428/1.1 |
| 6,685,996 B2 * | 2/2004 | Tarumi et al. ................ 428/1.1 |
| 6,929,833 B2 * | 8/2005 | Tarumi et al. ................ 428/1.1 |
| 7,029,731 B2 * | 4/2006 | Tarumi et al. ................ 428/1.1 |
| 7,033,652 B2 * | 4/2006 | Heckmeier et al. ........... 428/1.1 |
| 2002/0038859 A1 | 4/2002 | Heckmeier et al. |
| 2002/0061368 A1 | 5/2002 | Tarumi et al. |
| 2003/0186002 A1 * | 10/2003 | Heckmeier et al. ........... 428/1.1 |
| 2004/0006235 A1 * | 1/2004 | Pauluth et al. .............. 546/285 |
| 2005/0279968 A1 | 12/2005 | Manabe et al. |
| 2006/0216754 A1 | 9/2006 | Pauluth et al. |

FOREIGN PATENT DOCUMENTS

| | | |
|---|---|---|
| DE | 101 28 017 A1 | 3/2002 |
| EP | 0 439 089 A | 7/1991 |
| EP | 0 949 231 A | 10/1999 |
| EP | 1 346 995 A | 9/2003 |
| EP | 1 352 944 A | 10/2003 |
| WO | WO 89/02425 A | 3/1989 |
| WO | WO 2004/035710 A | 4/2004 |

* cited by examiner

*Primary Examiner*—Shean C Wu
(74) *Attorney, Agent, or Firm*—Millen, White, Zelano & Branigan, P.C.

(57) ABSTRACT

The invention relates to liquid-crystalline compounds of the formula I and to a liquid-crystalline medium based on a mixture of polar compounds, characterised in that it comprises one or more compounds of the formula I

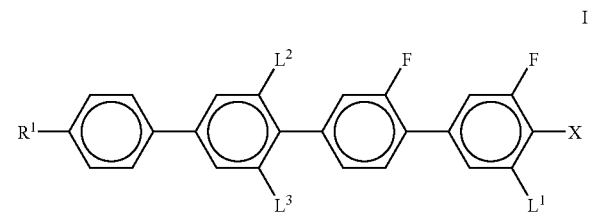

in which $R^1$, X, $L^1$, $L^2$ and $L^3$ have the meanings indicated in Claim 1.

20 Claims, No Drawings

LIQUID CRYSTALLINE MEDIUM

The present invention relates to liquid-crystalline compounds and to a liquid-crystalline medium, and to the use thereof for electro-optical purposes, and to displays containing this medium.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (superbirefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and relatively low vapour pressure are desired.

Furthermore, LCoS™ displays and displays based on a birefringence effect, such as OCB-displays, are interesting.

OCB displays (optically compensated bend) are based on a birefringence effect and contain a liquid-crystal layer having a so-called "bend" structure. The "bend" cell, also known as "pi" cell, was first proposed by P. Bos et al., SID 83 Digest, 30 (1983) for an electrically controllable λ/2 plate, whereas the OCB mode for displays was described by Y. Yamaguchi, T. Miyashita and T. Uchida, SID 93 Digest, 277 (1993), and then in papers by T. Miyashita et al. in, inter alia, Proc. Eurodisplay, 149 (1993), J. Appl. Phys. 34, L177 (1995), SID 95 Digest, 797 (1995), C.-L. Kuo et al., SID 94 Digest, 927 (1994) and M. Suzuki, SID 96 Digest, 618 (1996). An OCB cell contains a liquid-crystal cell having a "bend" alignment and a liquid-crystal medium of positive $\Delta\epsilon$. In addition, the OCB displays disclosed in the above-mentioned documents contain one or more birefringent optical retardation films for preventing undesired light transmission by the "bend" cell in the dark state. OCB displays have a number of advantages over conventional displays based on twisted nematic (TN) cells, such as, for example, a wider viewing angle and shorter response times.

The above-mentioned documents have shown that liquid-crystalline phases must have high values for the optical anisotropy $\Delta n$ and a relatively high positive value for the dielectric anisotropy $\Delta\epsilon$ and preferably quite low values for the ratio between the elastic constants $K_{33}/K_{11}$ and for the viscosity in order to be usable for high-information display elements based on the OCB effect. The industrial application of the OCB effect in electro-optical displays requires LC phases which have to satisfy a multiplicity of requirements. Particularly important here are chemical resistance to moisture, air and physical effects, such as heat, radiation in the infrared, visible and ultraviolet regions and direct and alternating electrical fields. Furthermore, LC phases which can be used industrially are required to have a liquid-crystalline mesophase in a suitable temperature range, relatively high birefringence, positive dielectric anisotropy and low viscosity.

LCoS™ (liquid crystal on silicon) displays are known from the prior art and are available from Three-Five Systems Inc. (Tempe, Ariz., USA). LCoS™ microdisplays are reflective displays which typically contain a liquid-crystal layer having a twisted nematic structure between a silicon backplane and a cover glass. The silicon backplane is an array of pixels, each of which has a mirrored surface which at the same time acts as electrical conductor. Each pixel comprises a stationary mirror covered by an active liquid-crystal layer having a twisted nematic alignment which can be switched into homeotropic alignment by application of a voltage. LCoS™ microdisplays are small, with a diagonal of typically less than 1.0", but enable high resolutions from ¼ VGA (78 thousand pixels) to UXGA+ (over 2 million pixels).

Owing to the small pixel size, LCoS™ displays also have a very small cell thickness, which is typically about 1 micron. The liquid-crystalline phases used in these displays therefore have to have, in particular, high values for the optical anisotropy $\Delta n$, in contrast to conventional reflective-type LC displays, which usually require LC phases of low $\Delta n$.

OCB mode and LCoS™ displays can be operated as matrix displays. Matrix liquid-crystal displays (MLC displays) are known. Examples of non-linear elements which can be used to individually switch the individual pixels are active elements (i.e. transistors). The term "active matrix" is then used, and a differentiation can be made between two types:

1. MOS (metal oxide semiconductor) or other diodes on silicon wafers as substrate,
2. Thin-film transistors (TFT) on a glass plate as substrate.

In the case of type 1, the electro-optical effect used is usually dynamic scattering or the guest/host effect.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not satisfy today's requirements.

In addition to liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterised by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence (Δn) is necessary in order to achieve low optical retardation (d. Δn). This low optical retardation results in usually acceptable low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

There thus continues to be a great demand for liquid-crystalline media for MLC, OCB, IPS, TN, LCoS or STN displays having high UV stability, relatively high ΔЄ values at the same time as a large working-temperature range, short response times even at low temperatures and low threshold voltage which do not have these disadvantages or only do so to a lesser extent.

In TN (Schadt-Helfrich) cells, media are desired which facilitate the following advantages in the cells:

extended nematic phase range (in particular down to low temperatures)

storage-stable, even at extremely low temperatures the ability to switch at extremely low temperatures (outdoor use, automobiles, avionics)

increased resistance to UV radiation (longer life)

higher optical anisotropies for faster response times owing to thinner cell thicknesses (d·Δn)

The media available from the prior art do not enable these advantages to be achieved while simultaneously retaining the other parameters.

In the case of supertwisted cells (STN), media are desired which facilitate greater multiplexability and/or a lower threshold voltage and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention is based on the object of providing media, in particular for MLC, OCB, IPS, LCoS, TN or STN displays of this type, which do not have the above-mentioned disadvantages or only do so to a lesser extent, and preferably at the same time have relatively high clearing points, low thresholds and relatively low rotational viscosities $\gamma_1$. The mixtures should furthermore be distinguished by high UV stability.

It has now been found that this object can be achieved if media according to the invention are used in displays. The media according to the invention are distinguished by their high UV stability. At the same time, the media have very low threshold voltages and relatively low rotational viscosities $\gamma_1$.

The invention thus relates to a liquid-crystalline medium based on a mixture of polar compounds, characterised in that it comprises one or more compounds of the formula I

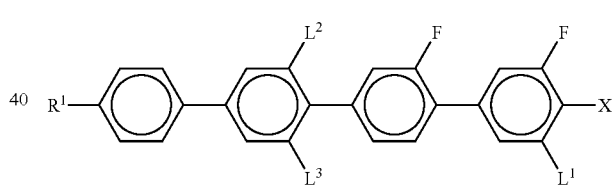

in which $R^1$ denotes a halogenated or unsubstituted alkyl or alkoxy radical having 1 to 15 C atoms, where one or more $CH_2$ groups in these radicals may also each, independently of one another, be replaced by

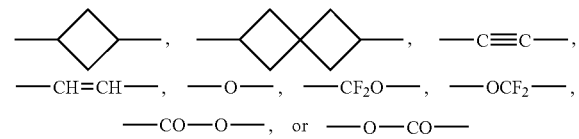

in such a way that O atoms are not linked directly to one another,

X denotes F, Cl, CN, $SF_5$, SCN, NCS, a halogenated alkyl radical, a halogenated alkenyl radical, a halogenated alkoxy radical or a halogenated alkenyloxy radical having up to 6 C atoms, and $L^1$, $L^2$ and $L^3$ each, independently of one another, denote H or F.

Surprisingly, it has been found that liquid-crystalline mixtures comprising compounds of the formula I have high clearing points and relatively low thresholds. The invention also relates to some compounds of the formula I, according to Claims 13 and 14. Particular preference is given to compounds in which $L^1$=F and $L^2$=$L^3$=H. Very particular preference is given to compounds in which $L^1$=F, $L^2$=$L^3$=H and X=F, $OCF_3$ or $OCHF_2$. X preferably denotes CN, F, $SF_5$, $OCHF_2$, $OC_2F_5$, $OC_3F_7$, NCS, $OCHFCF_3$, $OCF_2CHFCF_3$, $OCF_3$.

Fluorinated quaterphenyls are described in the prior art, for example in U.S. Pat. No. 6,669,998 B2, U.S. Pat. No. 6,565,933 B2, U.S. Pat. No. 6,596,350 A2, WO 89/02884, WO 90/01056, WO 91/03450, EP 0 439 089 B1, DE 44 45 224, WO 98/235564, EP 1 302 523 A1, EP 1 346 995. However, the compounds according to the invention are not mentioned explicitly WO 2004/035 710 A1 discloses compounds of the formula

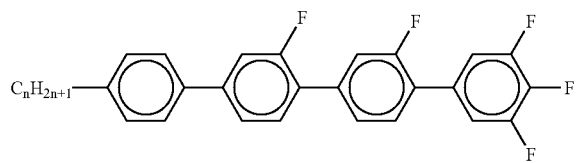

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or in order to optimise its threshold voltage and/or its viscosity. Surprisingly, the tetracyclic compounds according to the invention are very readily soluble. Thus, it is possible to prepare mixtures according to the invention which comprise 0.01-30.0% by weight, based on the mixture, of compounds of the formula I.

In the pure state, the compounds of the formula I are colourless and form liquid-crystalline mesophases in a temperature range which is favourably located for electro-optical use. They are stable chemically, thermally and to light.

If $R^1$ in the formula I denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^1$ denotes an alkyl radical in which one $CH_2$ group has been replaced by —CH=CH—, this may be straight-chain or branched. It is preferably straight-chain and has 2 to 10 C atoms. Accordingly, it denotes in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

If $R^1$ denotes an alkyl radical in which one $CH_2$ group has been replaced by —O— and one has been replaced by —CO—, these are preferably adjacent. These thus contain an acyloxy group —CO—O— or an oxycarbonyl group —O—CO—. These preferably denote straight-chain and have 2 to 6 C atoms. Accordingly, they are in particular acetoxy, propionyloxy, butyryoxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ denotes an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has 4 to 12 C atoms. Accordingly, it denotes in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

If $R^1$ denotes an alkyl or alkenyl radical which is monosubstituted by CN or $CF_3$, this radical is preferably straight-chain. The substitution by CN or $CF_3$ is in any desired position.

If $R^1$ denotes an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds containing branched wing groups $R^1$ may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

If $R^1$ represents an alkyl radical in which two or more $CH_2$ groups have been replaced by —O— and/or —CO—O—, this may be straight-chain or branched. It is preferably branched and has 3 to 12 C atoms. Accordingly, it denotes in particular biscarboxymethyl, 252-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis (methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)pentyl.

X in the compounds of the formulae preferably denote, independently of one another, F, Cl, CN, NCS, $CF_3$, $C_2F_5$, $C_3F_7$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CF_2H$, $OCClFCF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $CF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$, $CF=CHF$, $OCF=CHF$, in particular F, Cl, CN, NCS, $CF_3$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$ or $OCF_2CHFCF_3$.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I can be prepared, for example, as follows.

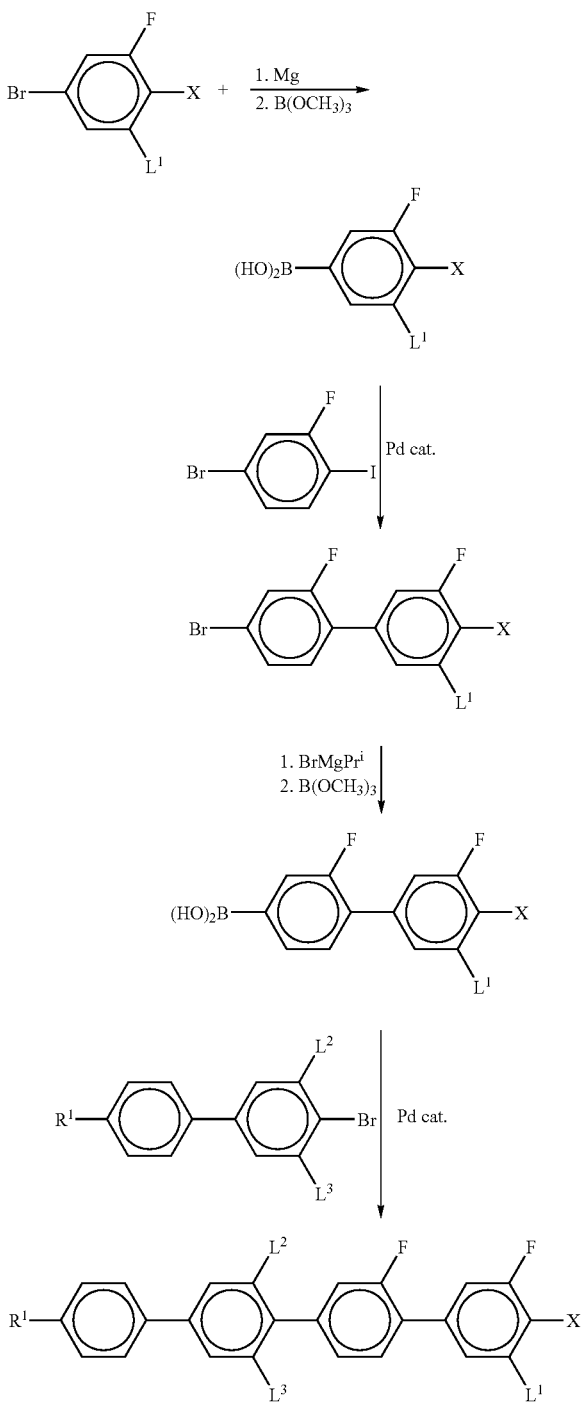

Scheme 1

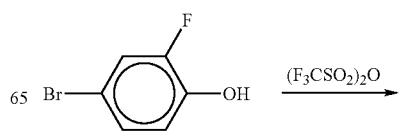

Scheme 2

-continued
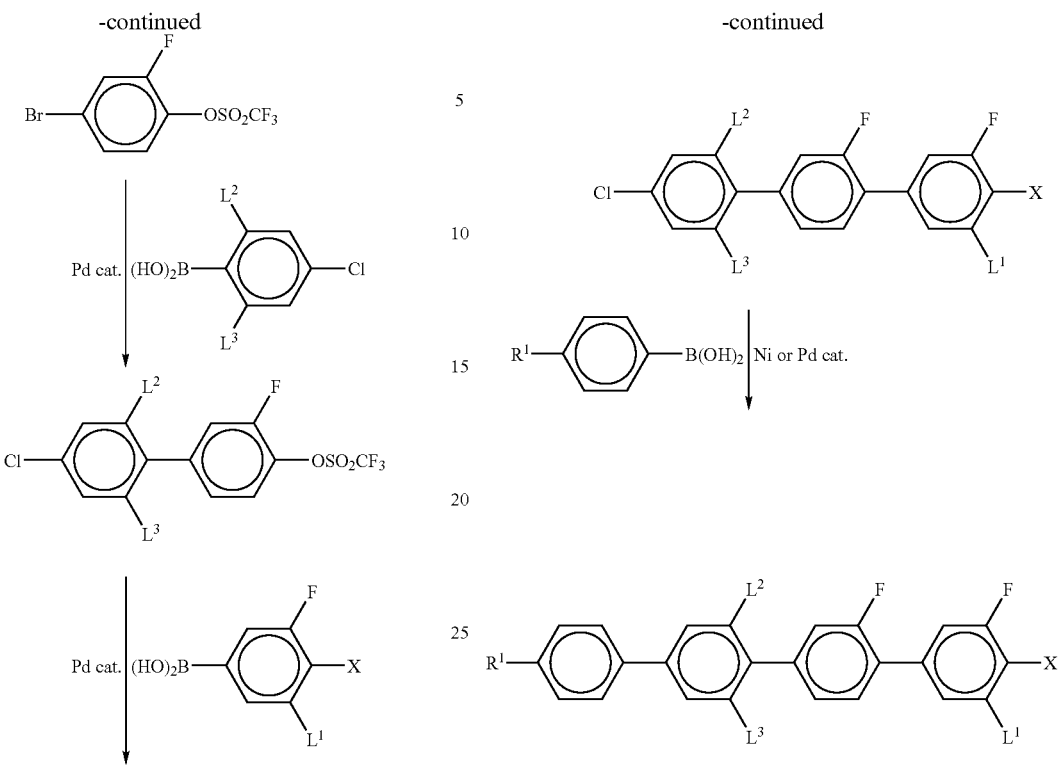
Scheme 3
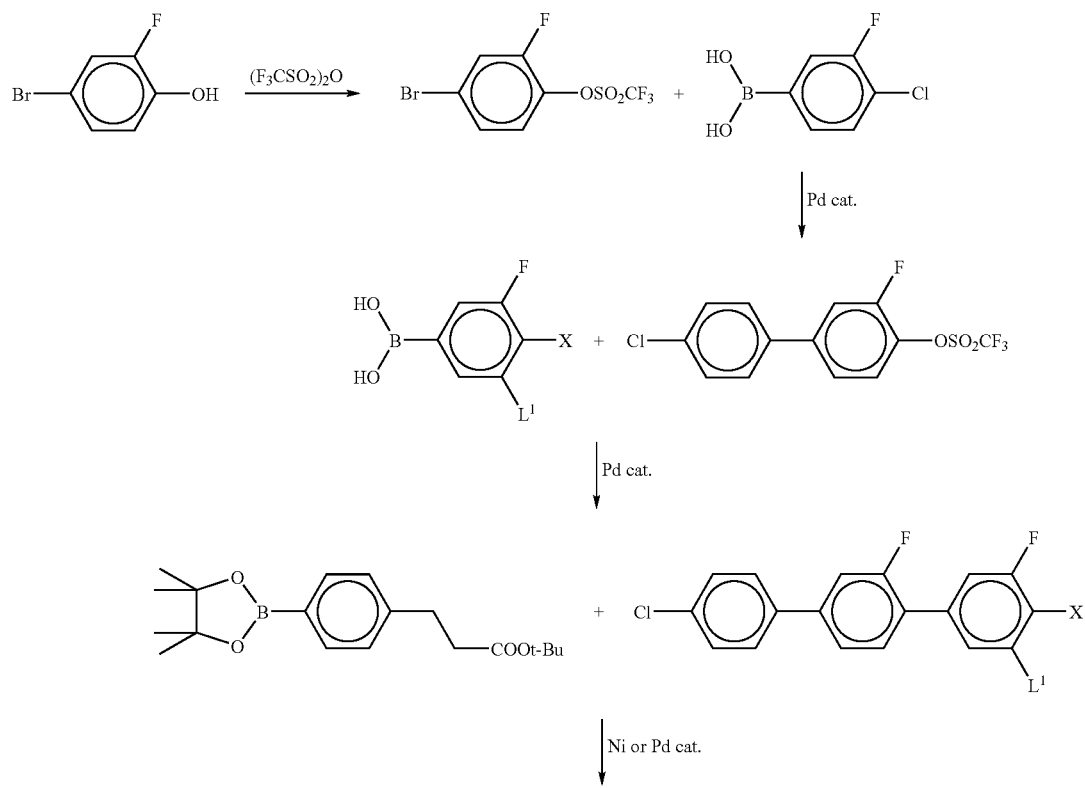

-continued

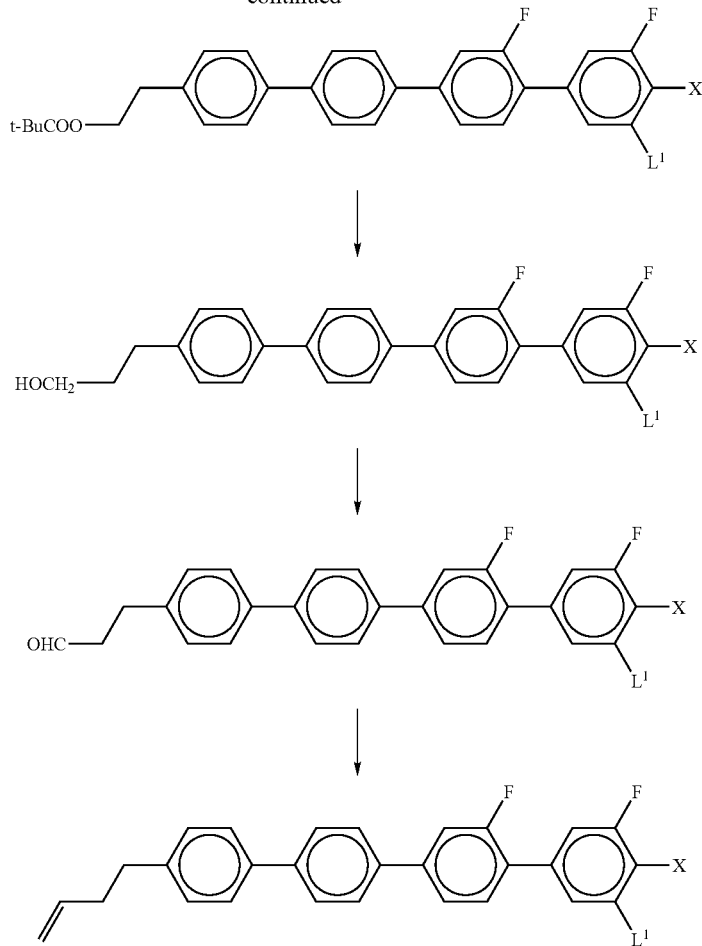

The invention also relates to electro-optical displays, in particular MLC displays, furthermore STN displays, having two plane-parallel outer plates, which, together with a frame, form a cell, integrated non-linear elements for switching individual pixels on the outer plates, and a nematic liquid-crystal mixture having very high optical anisotropy and high specific resistance which is located in the cell which contain media of this type, and to the use of these media for electro-optical purposes.

The mixtures according to the invention are particularly suitable for fast-switching monitors, TV/monitor combination units and high Δn TFT applications, such as, for example, projection television sets, LCoS and OCB.

The liquid-crystal mixtures according to the invention enable a significant widening of the available parameter latitude. The achievable combinations of clearing point, viscosity at low temperature, thermal and UV stability and high optical anisotropy are far superior to previous materials from the prior art.

The liquid-crystal mixtures according to the invention, while retaining the nematic phase down to −20° C. and preferably down to −30° C., particularly preferably down to −40° C., enable a clearing point above 60° C., preferably above 70° C., particularly preferably above 80° C., simultaneously dielectric anisotropy values Δ∈ of ≧4, preferably ≧5, and a high value for the specific resistance to be achieved, enabling excellent STN and MLC displays to be obtained. In particular, the mixtures are characterised by low operating voltages. The TN thresholds are below 2.5 V, preferably below 2.0 V, particularly preferably <1.8 V.

It goes without saying that, through a suitable choice of the components of the mixtures according to the invention, it is also possible for higher clearing points (for example above 110° C.) to be achieved at higher threshold voltages or lower clearing points to be achieved at lower threshold voltages with retention of the other advantageous properties. At viscosities correspondingly increased only slightly, it is likewise possible to obtain mixtures having higher Δ∈ and thus low thresholds. The MLC displays according to the invention preferably operate at the first Gooch and Tarry transmission minimum [C. H. Gooch and H. A. Tarry, Electron. Lett, 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $v_{20}$ at 20° C. is preferably <150 mm$^2$·s$^{-1}$, particularly preferably <120 mm$^2$·s$^{-1}$ and in particular <80 mm$^2$·s$^{-1}$. The rotational viscosity $\gamma_1$ of the mixtures according to the invention at 20° C. is preferably <200 mPa·s, particularly preferably <180 mPa·s. The nematic phase range is preferably at least 90°, in particular at least 100°. This range preferably extends at least from −20° to +80°.

A short response time is desired in liquid-crystal displays. This applies in particular to displays which are capable of video reproduction. For displays of this type, response times (total: $t_{on}+t_{off}$) of at most 25 ms are required. The upper limit for the response time is determined by the image refresh frequency. Besides the rotational viscosity $\gamma_1$, the tilt angle also influences the response time.

Measurements of the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than analogous mixtures comprising cyanophenylcyclohexanes of the formula

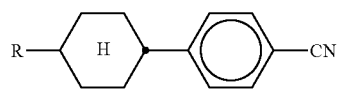

or esters of the formula

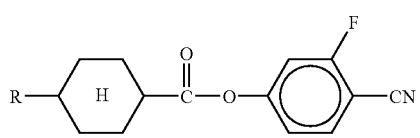

instead of the compounds of the formula I.

The UV stability of the mixtures according to the invention is considerably better, i.e. they exhibit a significantly smaller decrease in the HR on exposure to UV. Even low concentrations (<10% by weight) of the compounds of the formula I increase the HR in the mixtures by 6% or more compared with mixtures from the prior art.

Particularly preferred compounds of the formula I are compounds of the formulae I-1 to I-10:

I-1
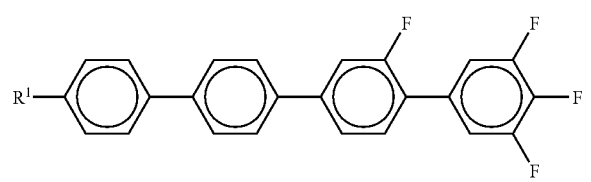

I-2
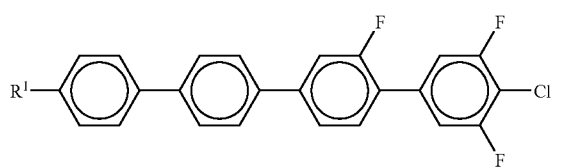

I-3
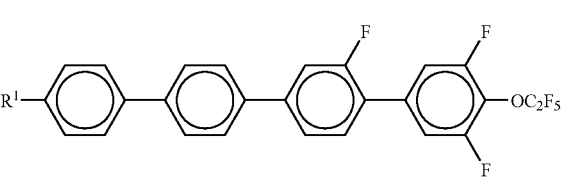

I-4
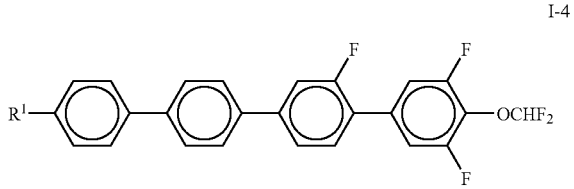

I-5
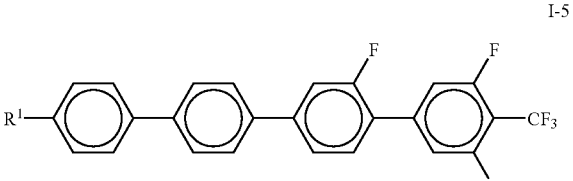

I-6
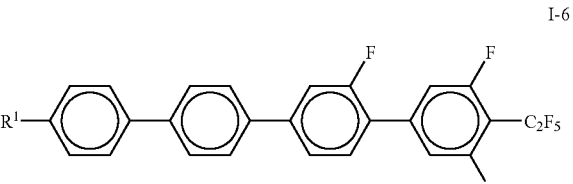

I-7
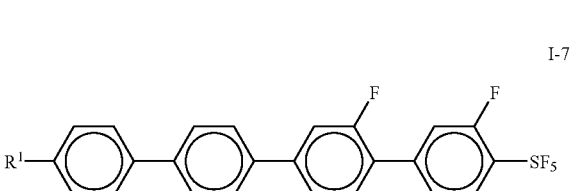

I-8
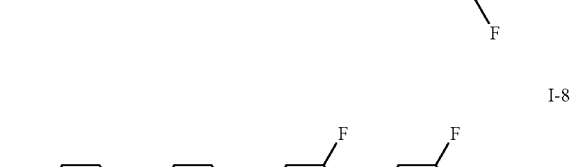

I-9

-continued

I-10

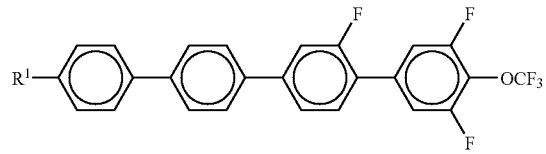

in which R¹ has the meaning indicated in the formula I. R¹ preferably denotes alkyl, furthermore alkenyl.

Of these preferred compounds, particular preference is given to those of the formulae I-1, I-4, I-7 and I-10, in particular those of the formulae I-1 and I-10.

R¹ in the formula I and in the sub-formulae II to I-10 preferably denotes $C_2H_5$, n-$C_3H_7$, n-$C_5H_{11}$, furthermore $CH_3$, n-$C_4H_9$, n-$C_6H_{13}$, n-$C_7H_{15}$, $CH_2$=CH, $CH_3CH$=CH, $CH_2$=$CHCH_2CH_2$ or $CH_3CH$=$CHCH_2CH_2$. R¹ very particularly preferably denotes n-$C_3H_7$.

Preferred embodiments are indicated below:

The medium comprises one, two or more compounds of the formulae I-1 to I-10;

The medium preferably comprises at least one of the following compounds

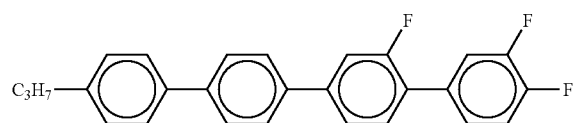

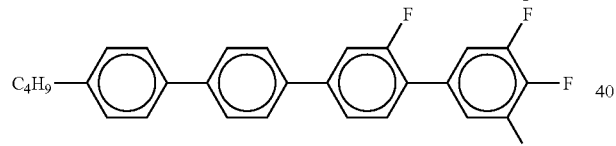

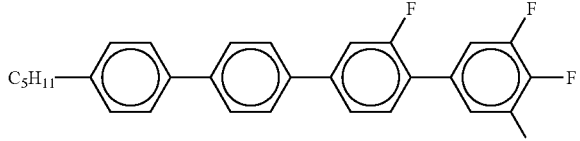

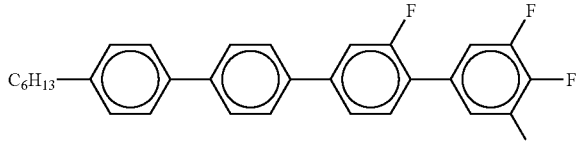

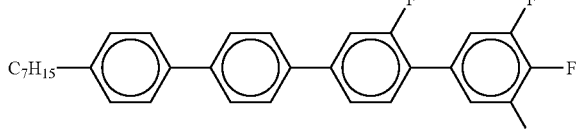

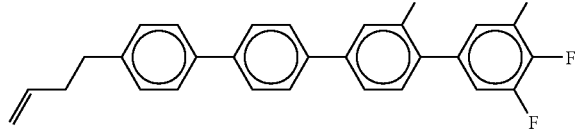

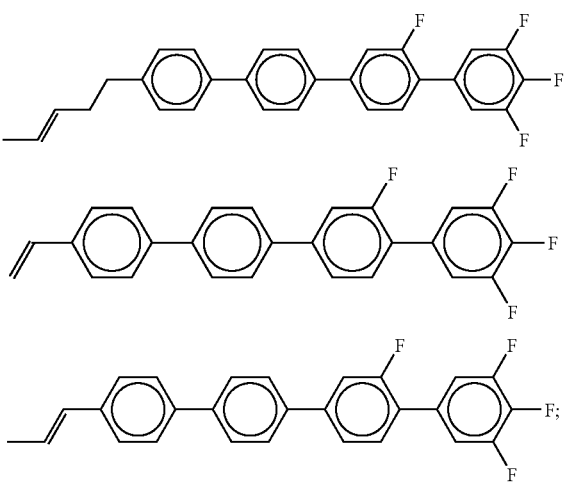

The medium preferably comprises one or more compounds of the formula I*

I*

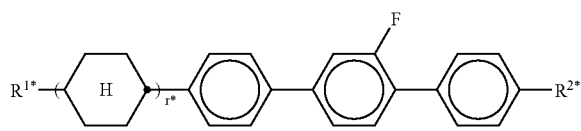

in which

R¹* and R²* each, independently of one another, denote alkyl, alkoxy, oxaalkyl, fluoroalkyl, alkenyloxy or alkenyl, each having up to 9 C atoms, r* denotes 0 or 1.

Particular preference is given to compounds of the formulae I*-1 to I*-8

I*-1

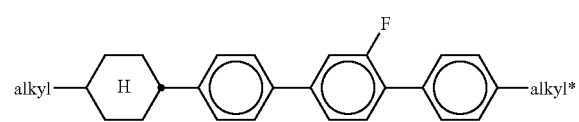

I*-2

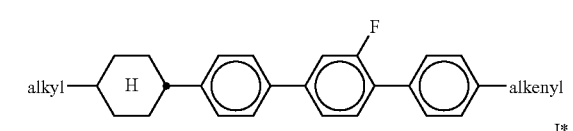

I*-3

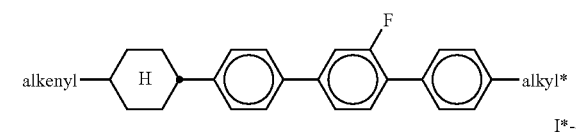

I*-4

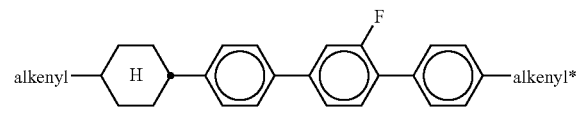

-continued

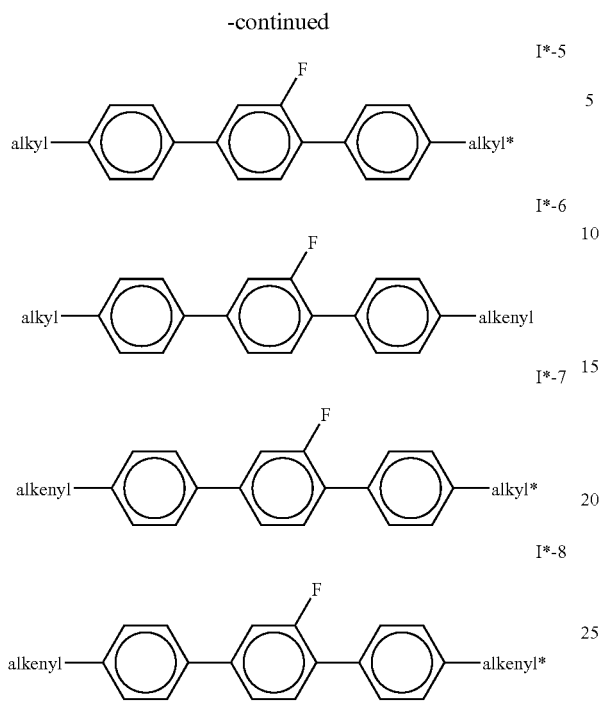

I*-5

I*-6

I*-7

I*-8 in which
alkyl and alkyl* each, independently of one another, denote straight-chain alkyl having 1-6 C atoms, and
alkenyl and alkenyl* each, independently of one another, denote straight-chain alkenyl having 2-6 C atoms.

Of the compounds I*-1 to I*-8, particular preference is given to the compounds I*-5 to I*-7. The compound I*-5 is very particularly preferred.

The medium comprises one, two, three or four compounds of the formula I*. The concentration of the compound(s) of the formula I* in the mixture according to the invention is 2-50% by weight, preferably 2-40% by weight, in particular 5-40% by weight.

The medium additionally comprises one or more compounds selected from the group consisting of the general formulae II to VI:

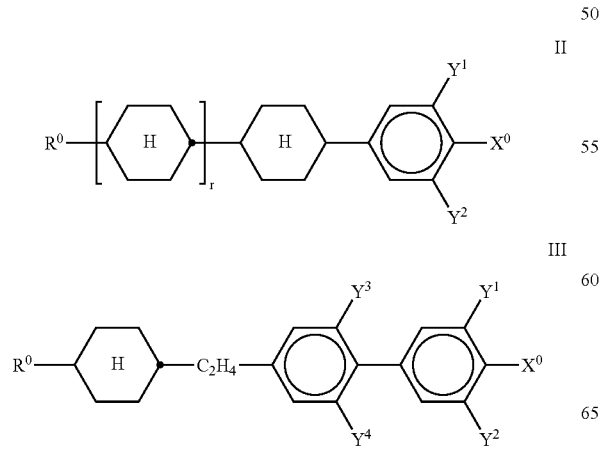

II

III

-continued

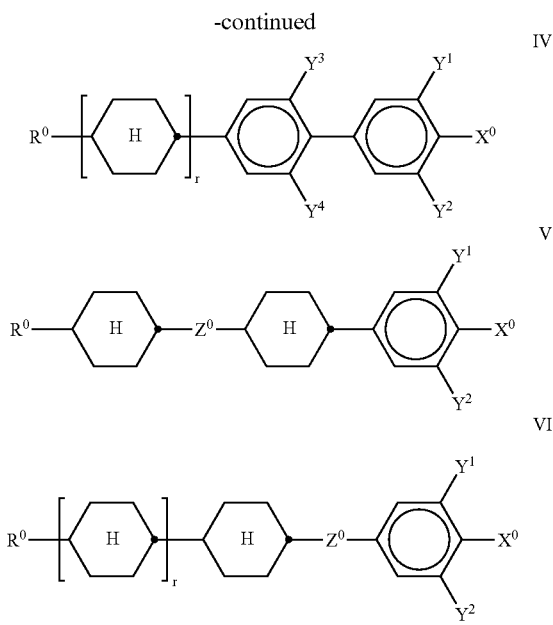

IV

V

VI in which the individual radicals have the following meanings;
$R^0$ alkyl, alkoxy, oxaalkyl, fluoroalkyl or alkenyl, each having up to 9 C atoms,
$X^0$ F, Cl, halogenated alkyl, halogenated alkenyl, halogenated oxaalkyl, halogenated alkenyloxy or halogenated alkoxy having up to 6 C atoms,
$Z^0$ —$C_2F_4$—, —CF=CF—, —$C_2H_4$—, —CH=CH—, —$(CH_2)_4$—, —$OCH_2$—, —$CH_2O$—, —$CF_2O$— or —$OCF_2$—,
$Y^1$ to $Y^4$ each, independently of one another, H or F,
r 0 or 1.

The compound of the formula IV is preferably

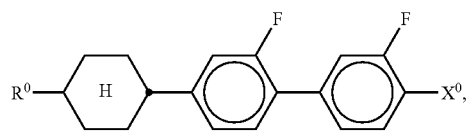

IVa

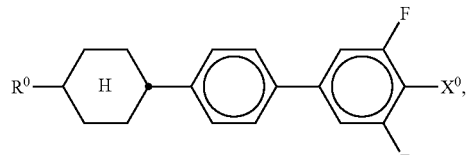

IVb

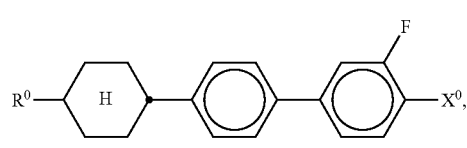

IVc

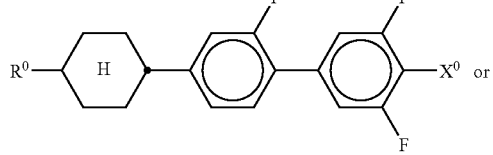

IVd

-continued

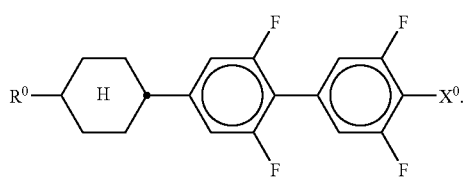
IVe

The medium additionally comprises one or more compounds selected from the group consisting of the general formulae VII to XII:

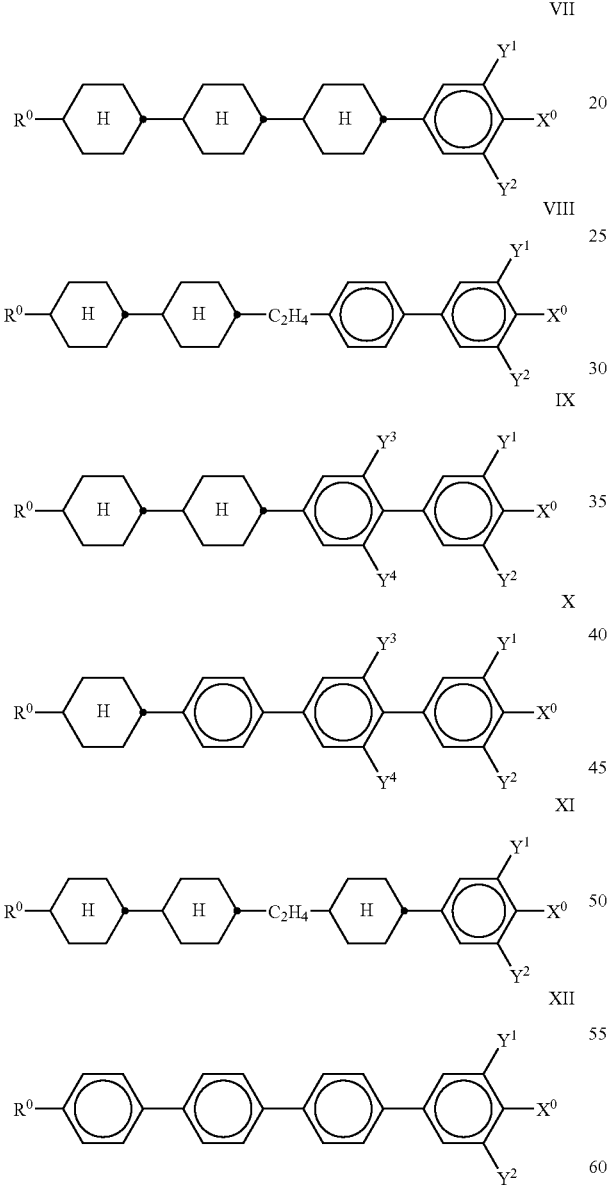

in which $R^0$, $X^0$ and $Y^{1-4}$ each, independently of one another, have one of the meanings indicated in claim 8. $X^0$ is preferably F, Cl, $CF_3$, $OCF_3$ or $OCHF_2$. $R^0$ preferably denotes alkyl, alkoxy, oxaalkyl, fluoroalkyl or alkenyl, each having up to 6 C atoms.

The medium additionally comprises one or more compounds of the formulae E-a to E-d

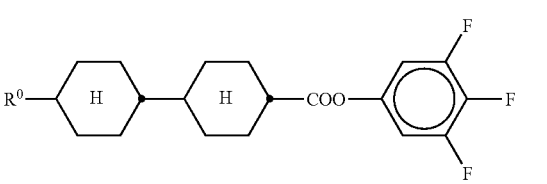
E-a

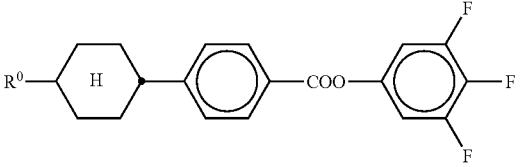
E-b

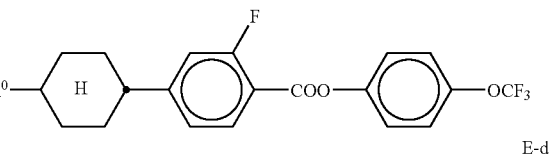
E-c

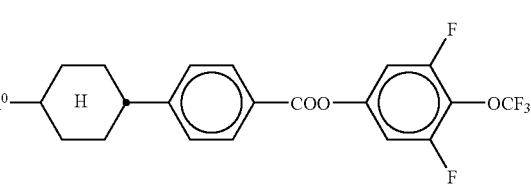
E-d in which $R^0$ has the meanings indicated in Claim 8.

The proportion of the compounds of the formulae E-a to E-d is preferably 10-30% by weight, in particular 15-25% by weight.

The proportion of compounds of the formulae I and I* together in the mixture as a whole is at least 5% by weight, preferably ≧10% by weight and in particular ≧15% by weight.

The proportion of compounds of the formula I in the mixture as a whole is 0.01 to 30% by weight, particularly preferably 0.5 to 20% by weight.

The proportion of compounds of the formulae II to VI in the mixture as a whole is 10 to 80% by weight.

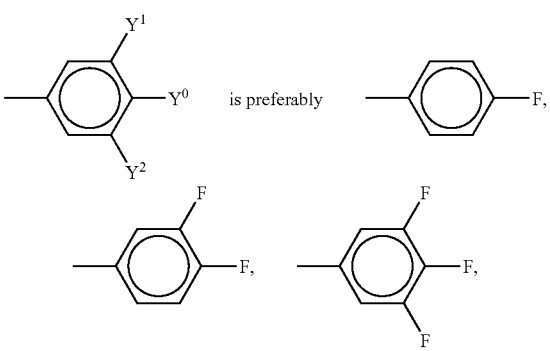

-continued

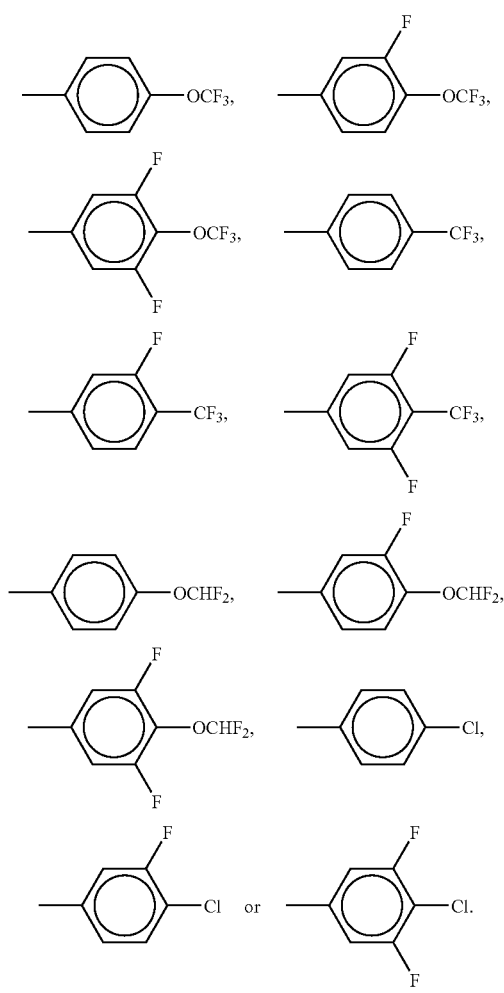

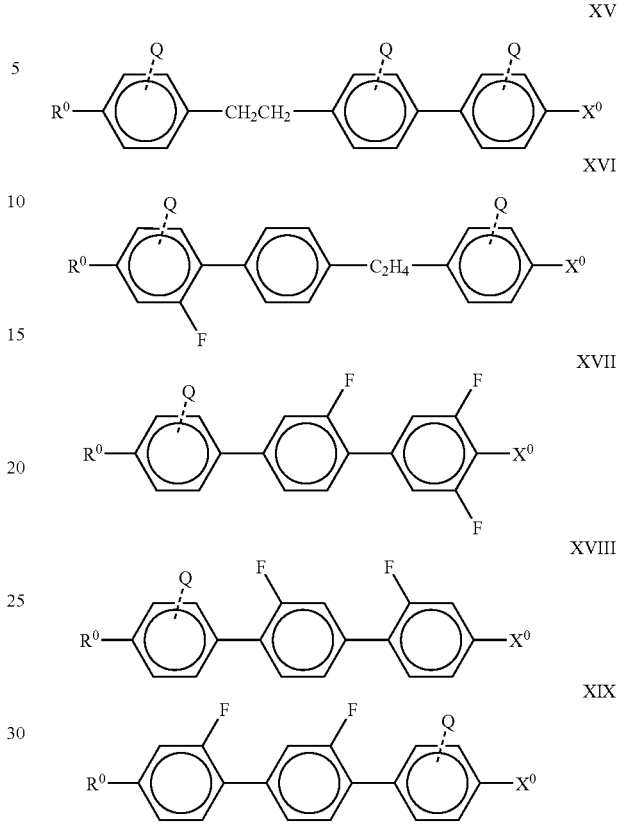

in which $R^0$ and $X^0$ have the meanings indicated above, $Y^1$ is H or F, and Q is zero, one or more substituents Cl or F, $X^0$ preferably denotes F or Cl. The concentration of the compounds of the formulae XIII to XIX is preferably 0.05-30% by weight, in particular 1-25% by weight.

The medium preferably comprises 5-35% by weight of the compound IVa.

The medium preferably comprises one, two or three compounds of the formula IVa in which $X^0$ denotes F or $OCF_3$.

The medium preferably comprises one or more compounds of the formulae IIa to IIg

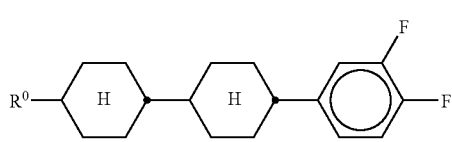

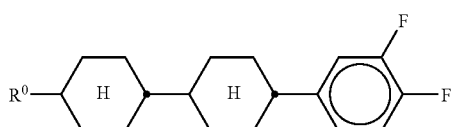

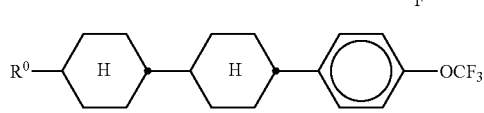

The medium comprises compounds of the formulae II, III, IV, V and/or VI.

$R^0$ in the compounds of the formulae II to XIX is preferably straight-chain alkyl or alkenyl having 2 to 7 C atoms.

The medium essentially consists of compounds of the formulae I, I* and XIII to XIX, where essentially means ≧50% by weight.

The medium comprises further compounds, preferably selected from the following group consisting of the general formulae XIII to XIX:

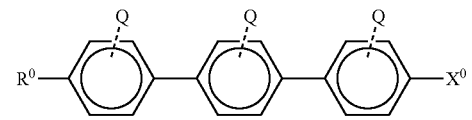

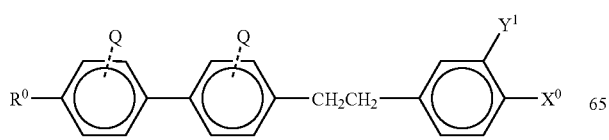

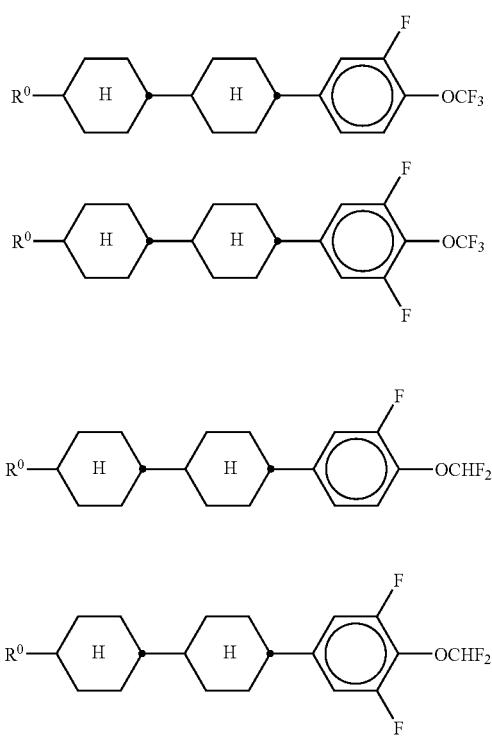

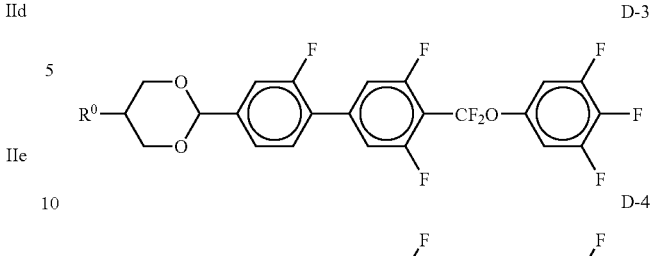

in which $R^0$ has the meanings indicated above.

The proportion of the dioxane compounds D-1 to D-4 in the mixtures according to the invention is preferably 0-30% by weight, in particular 5-25% by weight and very particularly preferably 8-20% by weight.

The medium additionally comprises one, two or more bicyclic compounds of the formulae Z-1 to Z-8 in which $R^0$ has the meanings indicated above. In the compounds of formulae IIa-IIg, $R^0$ preferably denotes methyl, ethyl, n-propyl, n-butyl and n-pentyl.

The weight ratio I or I+I*: (II+III+IV+V+VI) is preferably 1:10 to 10:1.

The medium essentially consists of compounds selected from the group consisting of the general formulae I to XIX.

The proportion of the compounds of the formulae IVb, IVc and/or IVd in which $X^0$ denotes fluorine and $R^0$ denotes $CH_3$, $C_2H_5$, n-$C_3H_7$, n-$C_4H_9$ or n-$C_5H_{11}$ in the mixture as a whole is 2 to 25% by weight, in particular 2 to 20% by weight.

The medium preferably comprises one, two or more, preferably one, two or more dioxane compounds of the formulae D-1 to D-4

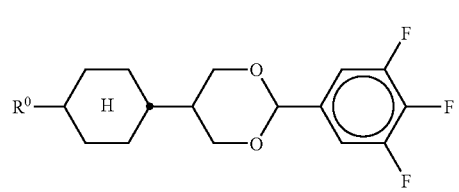

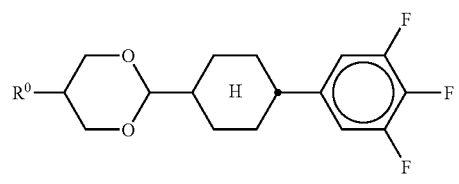

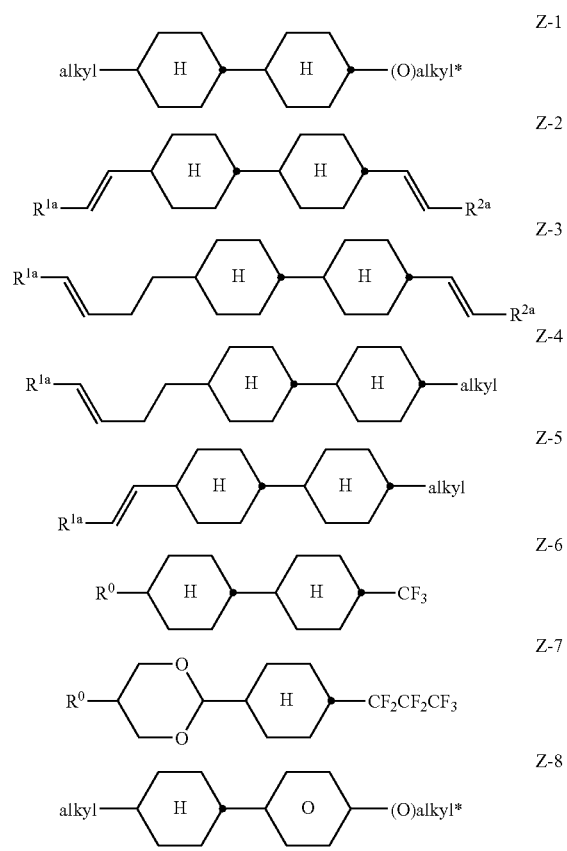

in which $R^{1a}$ and $R^{2a}$ each, independently of one another, denote H, $CH_3$, $C_2H_5$ or n-$C_3H_7$ Alkyl and alkyl* each, independently of one another, denote a straight-chain or branched alkyl chain having 1-7 C atoms. $R^0$ has the meanings indicated above. In the compounds Z-6 and Z-7, $R^0$ preferably denotes straight-chain alkyl or alkenyl.

Of the said bicyclic compounds, particular preference is given to the compounds of the formulae Z-1, Z-2, Z-5, Z-6 and Z-8.

The medium additionally comprises one, two or more compounds having fused rings of the formulae AN1 to AN11:

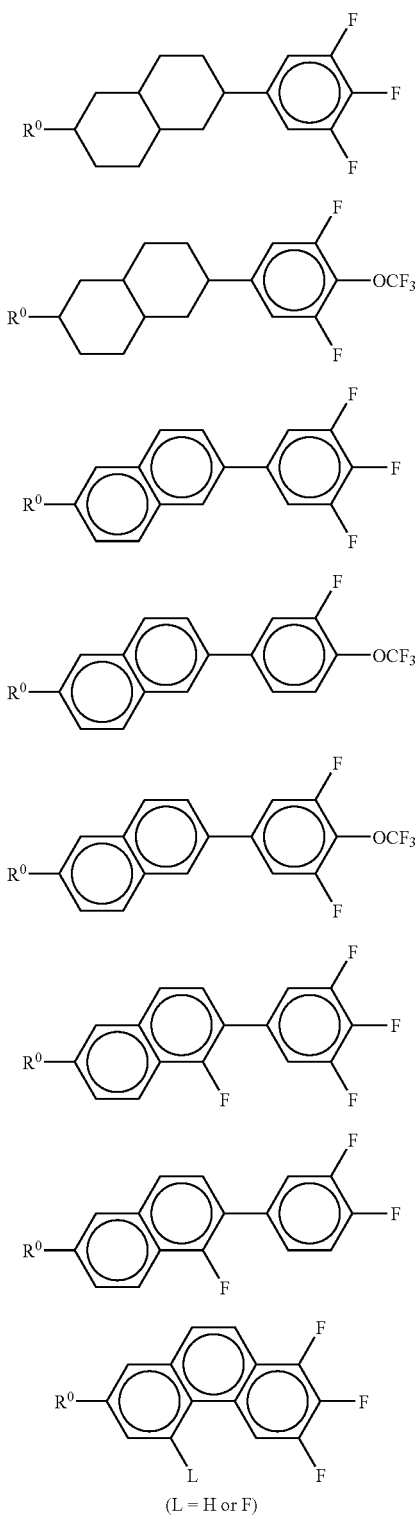

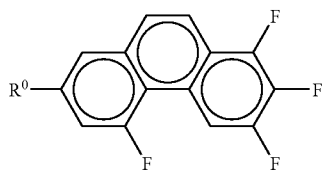

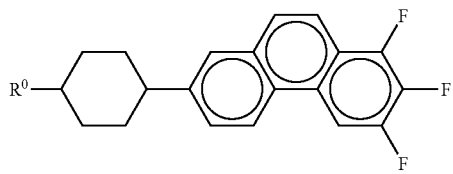

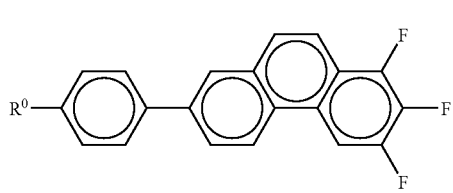

in which $R^0$ has the meanings indicated above.

The mixtures according to the invention are distinguished, in particular, by the fact that they have clearing points of >75° C. and thresholds of <2.0 V.

It has been found that even a relatively small proportion of compounds of the formulae I and I* mixed with conventional liquid-crystal materials, but in particular with one or more compounds of the formulae II, III, IV, V, VI, XIII, XIV, XV, XVI, XVII, XVIII and/or XIX, results in a significant reduction in the threshold voltage, with broad nematic phases having low smectic-nematic transition temperatures being observed at the same time, improving the storage stability. At the same time, the mixtures exhibit very good values for the VHR on UV exposure.

The term "alkyl" or "alkyl*" encompasses straight-chain and branched alkyl groups having 1-7 carbon atoms, in particular the straight-chain groups methyl, ethyl, propyl, butyl, pentyl, hexyl and heptyl. Groups having 1-6 carbon atoms are generally preferred.

The term "alkenyl" encompasses straight-chain and branched alkenyl groups having 2-7 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxy" preferably encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa. Higher values for $K_1$ facilitate faster response times.

The optimum mixing ratio of the compounds of the formulae I and II+III+IV+V+VI depends substantially on the desired properties, on the choice of the components of the formulae I, II, III, IV, V and/or VI, and on the choice of any further components that may be present.

Suitable mixing ratios within the range indicated above can easily be determined from case to case.

The total amount of compounds of the formulae I* and I to XIX in the mixtures according to the invention is not crucial. The mixtures can therefore comprise one or more further components for the purposes of optimisation of various properties. However, the observed effect on the addressing times and the threshold voltage is generally greater, the higher the total concentration of compounds of the formulae I* and I to XIX.

In a particularly preferred embodiment, the media according to the invention comprise compounds of the formulae II to VI (preferably II, III and/or IV, in particular IVa) in which $X^0$ denotes F, $OCF_3$, $OCHF_2$, $OCH=CF_2$, $OCF=CF_2$ or $OCF_2$—$CF_2H$. A favourable synergistic effect with the compounds of the formula I results in particularly advantageous properties. In particular, mixtures comprising compounds of the formulae I, I* and IVa are distinguished by their low threshold voltage.

The individual compounds of the formulae I, I* and II to XIX and the sub-formulae thereof which can be used in the media according to the invention are either known or can be prepared analogously to the known compounds.

The construction of the MLC display according to the invention from polarisers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

A significant difference between the displays according to the invention and the hitherto conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilisers, such as Tinuvin® from Ciba, antioxidants, free-radical scavengers, etc. For example, 0-15% of pleochroic dyes or chiral dopants can be added. Suitable stabilisers and dopants are mentioned below in Tables C and D.

C denotes a crystalline phase, S a smectic phase, $S_c$ a smectic C phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2.0 times the value of $V_{10}$. $\Delta n$ denotes the optical anisotropy. $\Delta\in$ denotes the dielectric anisotropy ($\Delta\in=\in_\parallel-\in_\perp$, where $\in_\parallel$ denotes the dielectric constant parallel to the longitudinal molecular axes and $\in_\perp$ denotes the dielectric constant perpendicular thereto). The electro-optical data are measured in a TN cell at the 1st minimum (i.e. at a d·Δn value of 0.5 μm) at 20° C., unless expressly stated otherwise. The optical data are measured at 20° C., unless expressly stated otherwise.

In the present application and in the examples below, the structures of the liquid-crystal compounds are indicated by means of acronyms, the trans-formation into chemical formulae taking place in accordance with Tables A and B below. All radicals $C_nH_{2n+1}$ and $C_mH_{2m+1}$ are straight-chain alkyl radicals having n and m C atoms respectively; n and m are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |

-continued
| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nmF | $C_nH_{2n+1}$ | $C_mH_{2m+1}$ | F | H |
| nOCF$_3$ | $C_nH_{2n+1}$ | OCF$_3$ | H | H |
| nOCF$_3$.F | $C_nH_{2n+1}$ | OCF$_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |
Preferred mixture components are given in Tables A and B.
TABLE A
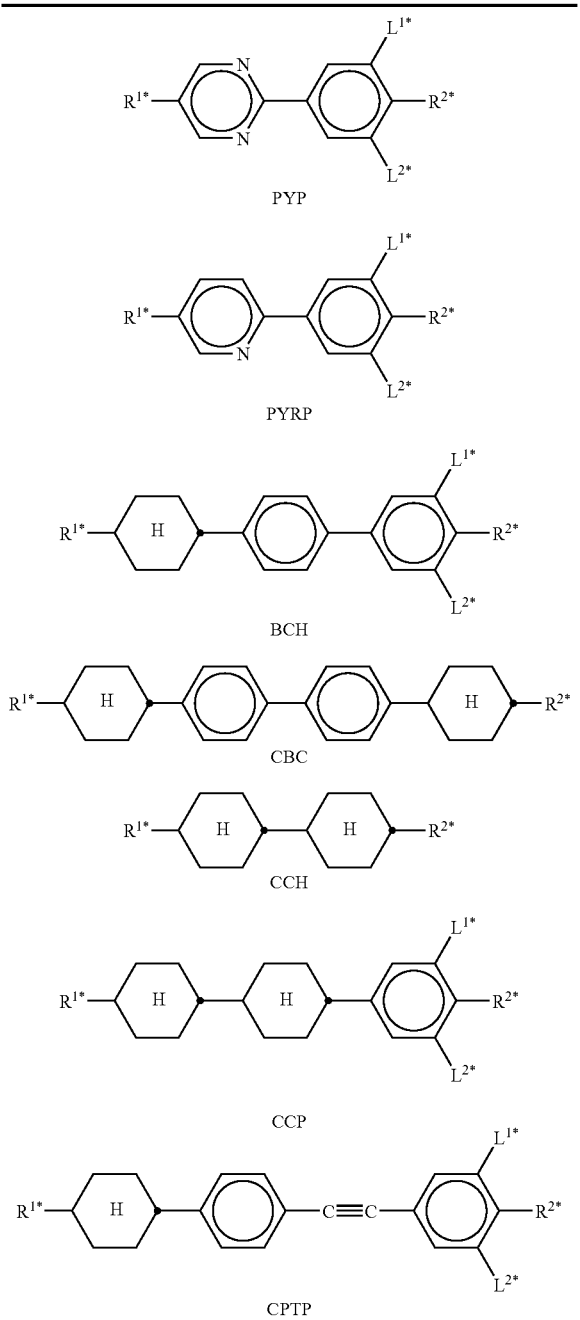
TABLE A-continued
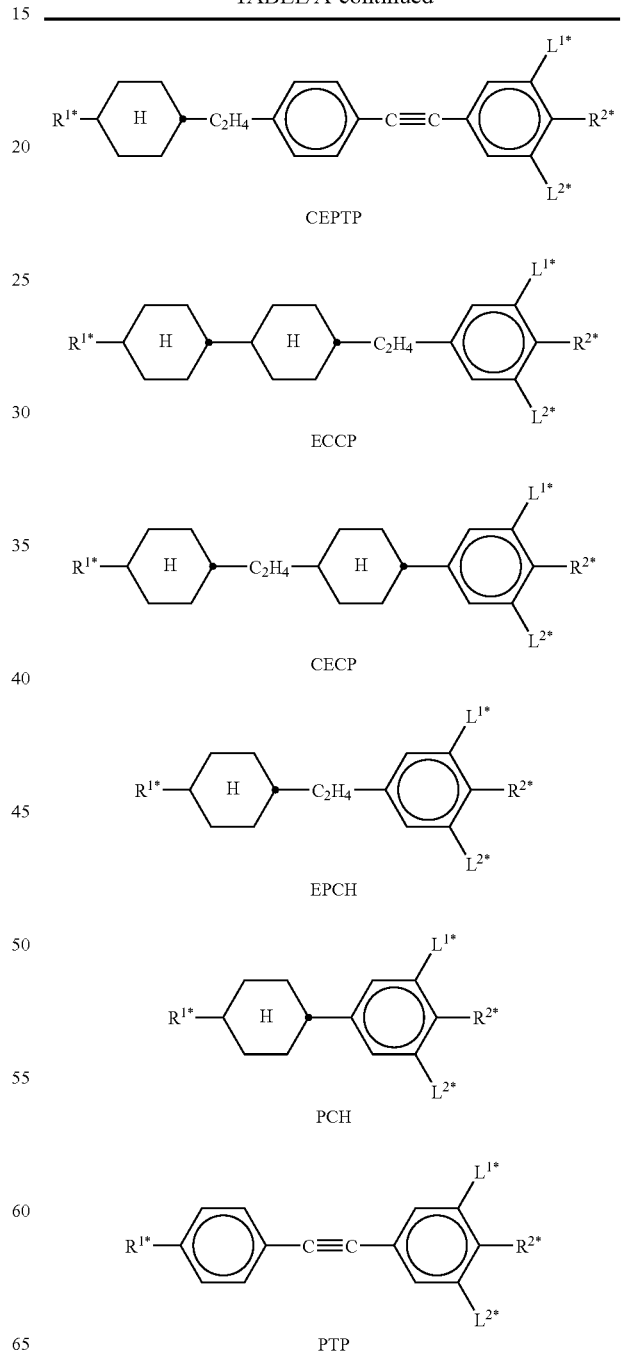

TABLE A-continued
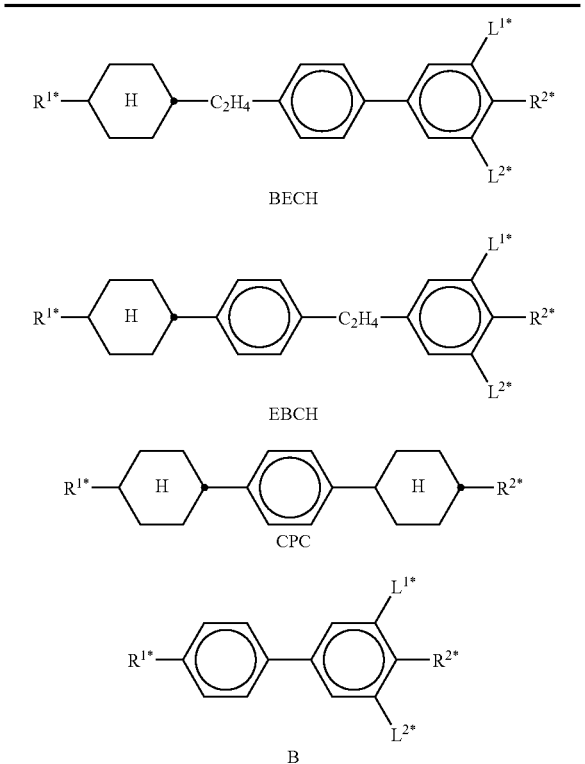
TABLE A-continued
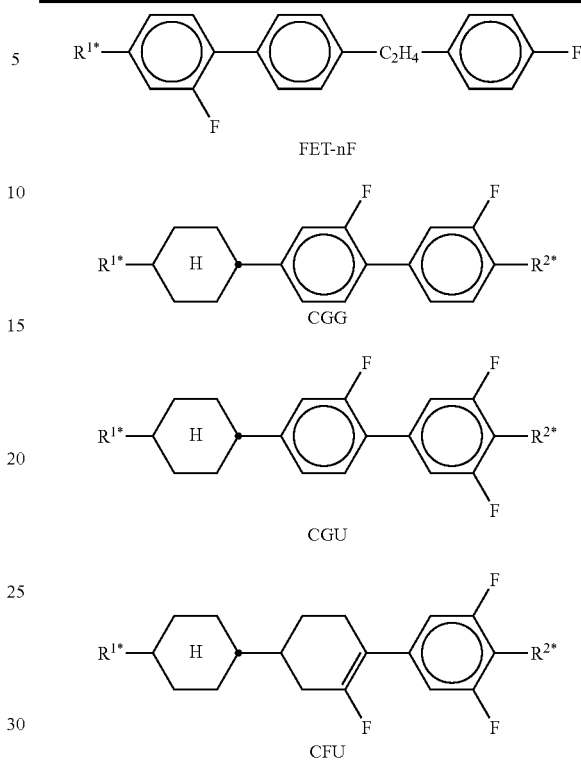
TABLE B
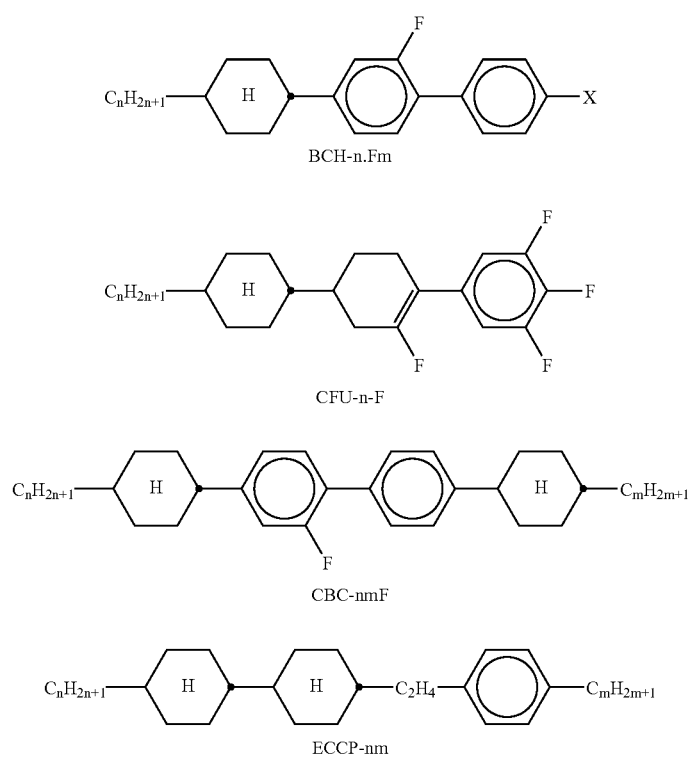

TABLE B-continued
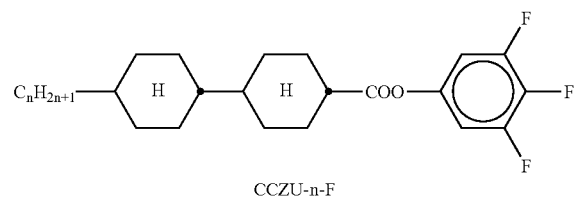
CCZU-n-F
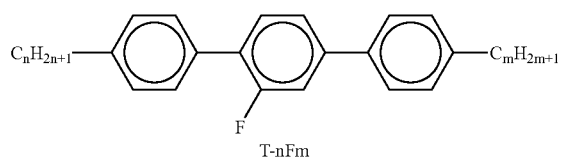
T-nFm
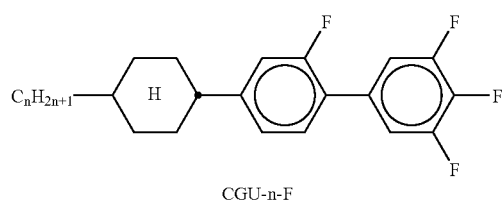
CGU-n-F
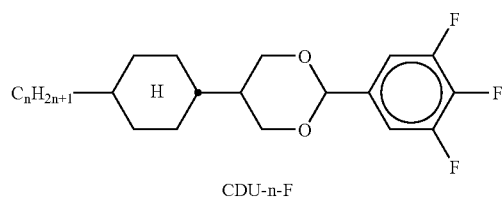
CDU-n-F
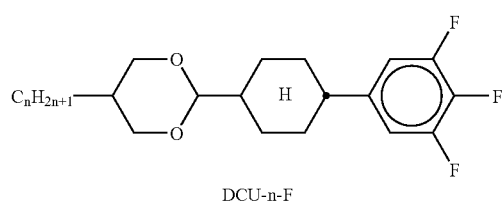
DCU-n-F
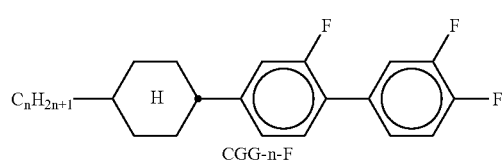
CGG-n-F
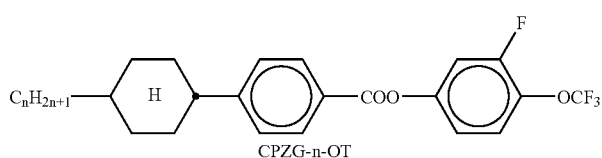
CPZG-n-OT
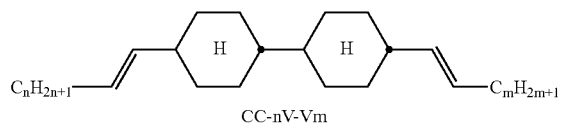
CC-nV-Vm
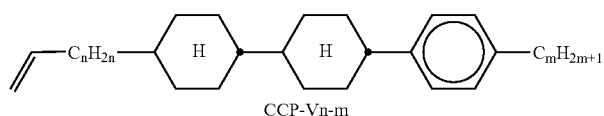
CCP-Vn-m TABLE B-continued
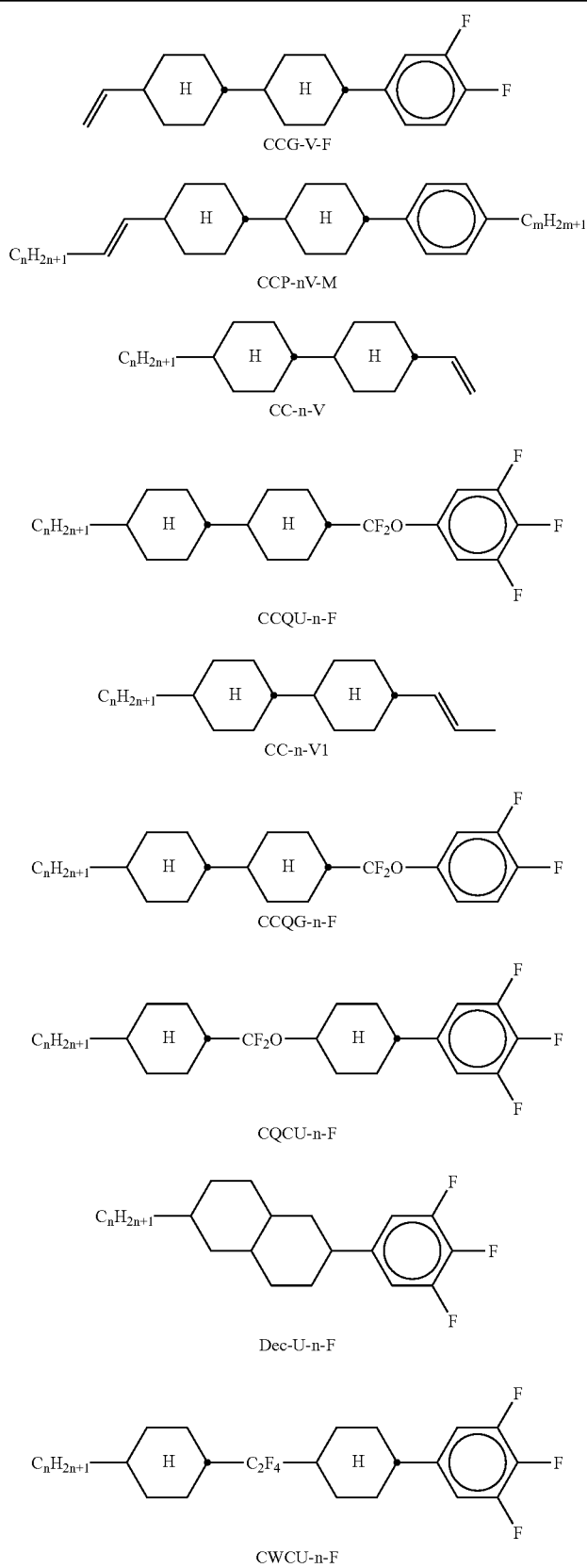

TABLE B-continued
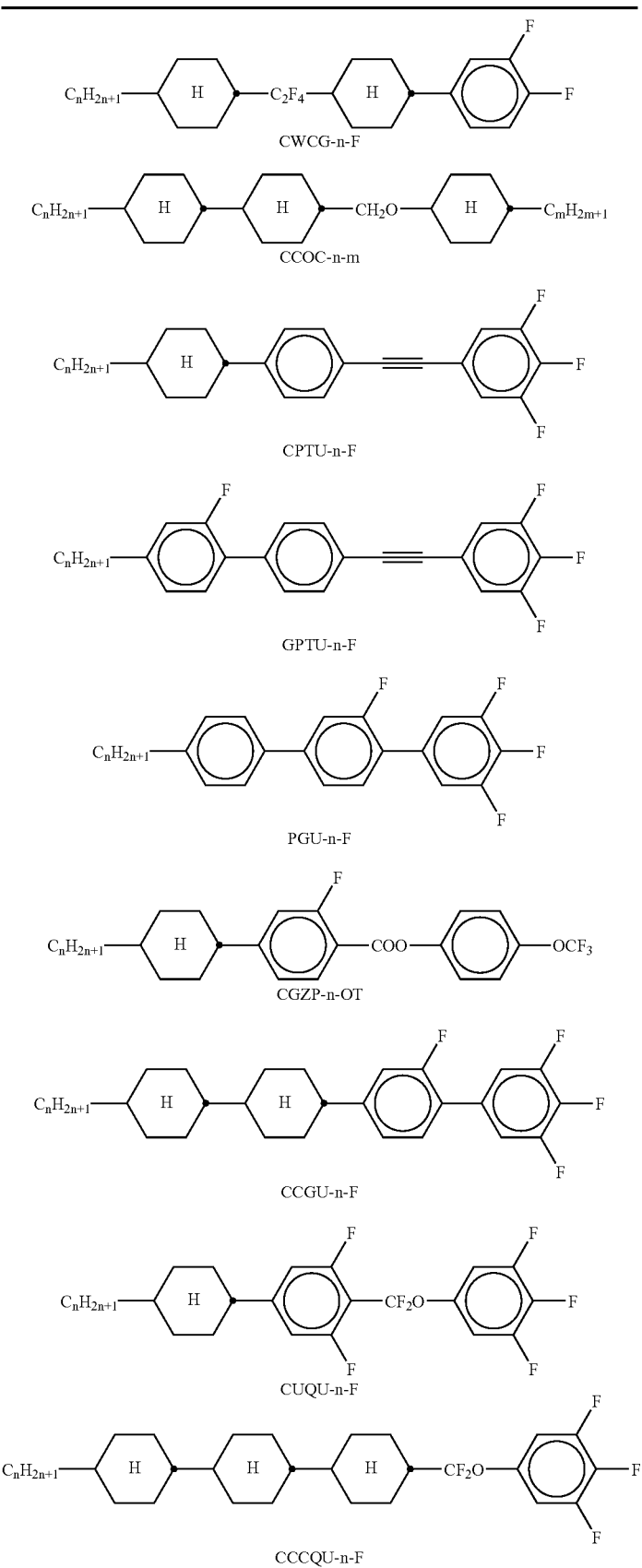

TABLE B-continued

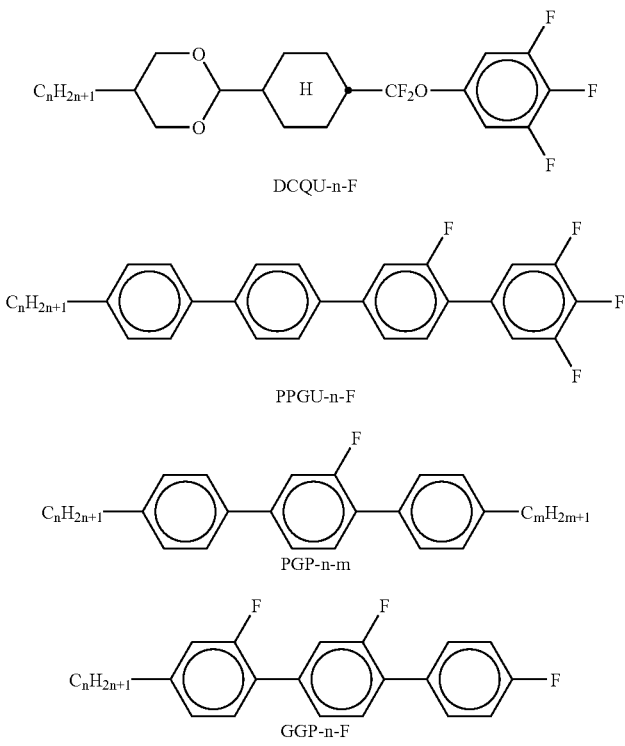

Particular preference is given to liquid-crystalline mixtures which, besides the compounds of the formula II, comprise at least one, two, three, four or more compounds from Table B.

TABLE C

Table C shows possible dopants which are generally added to the mixtures according to the invention. The mixtures preferably comprise 0-10% by weight, in particular 0.01-5% by weight and particularly preferably 0.01-3% by weight of dopants.

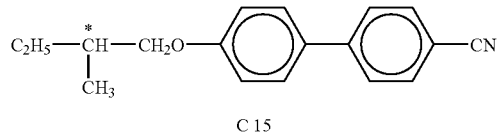

C 15

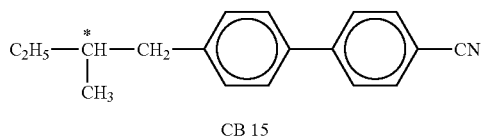

CB 15

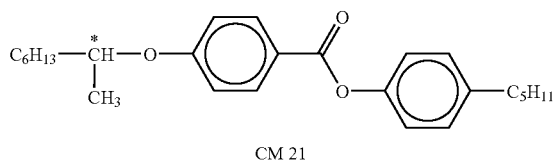

CM 21

TABLE C-continued
Table C shows possible dopants which are generally added to the mixtures according to the invention. The mixtures preferably comprise 0-10% by weight, in particular 0.01-5% by weight and particularly preferably 0.01-3% by weight of dopants.
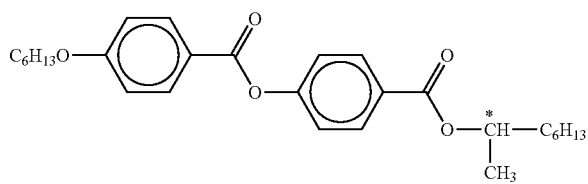
R/S-811
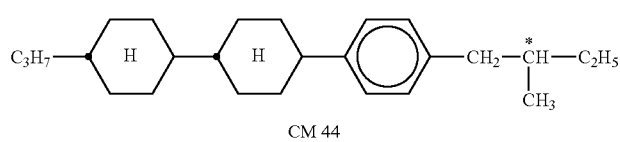
CM 44
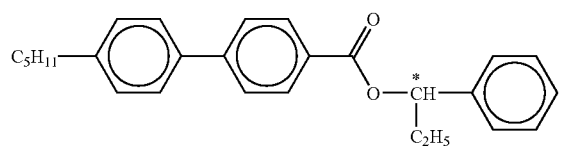
CM 45
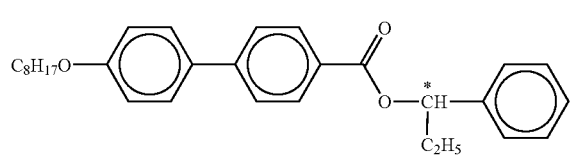
CM 47
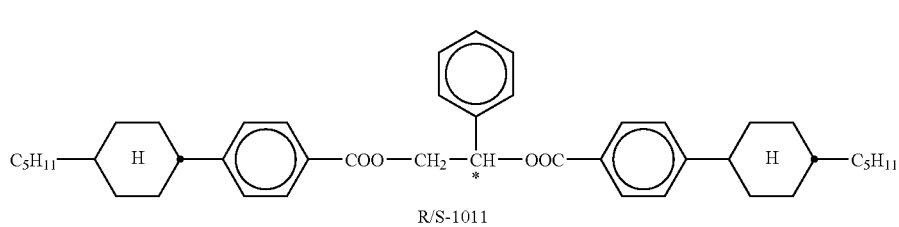
R/S-1011
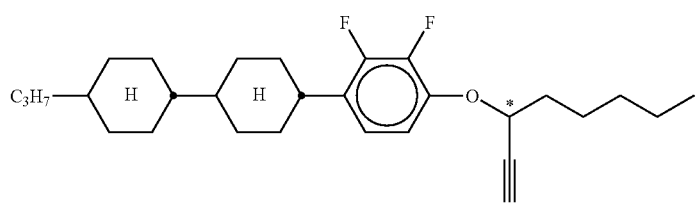
R/S-3011
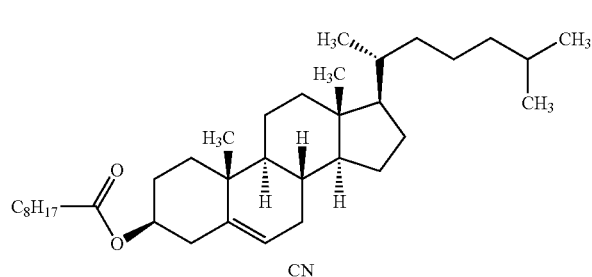
CN TABLE C-continued Table C shows possible dopants which are generally added to the mixtures according to the invention. The mixtures preferably comprise 0-10% by weight, in particular 0.01-5% by weight and particularly preferably 0.01-3% by weight of dopants.

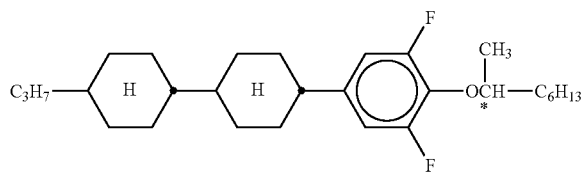

R/S-2011

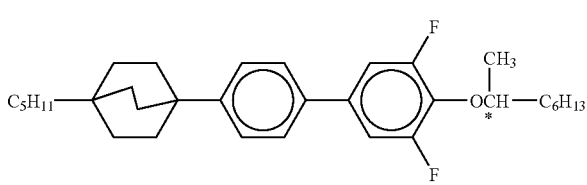

R/S-4011

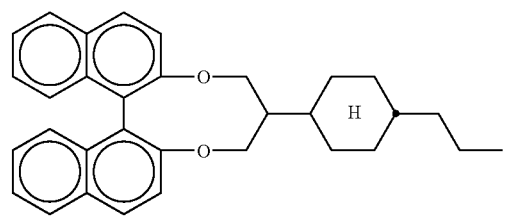

R/S-5011

TABLE D

Stabilisers which can be added, for example, to the mixtures according to the invention in amounts of 0-10% by weight are mentioned below.

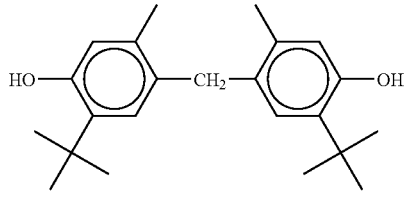

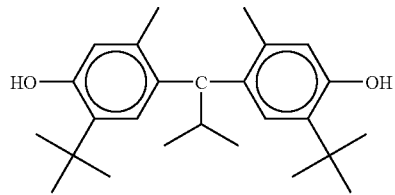

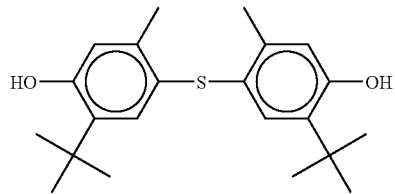

TABLE D-continued
Stabilisers which can be added, for example, to the mixtures according to the invention in amounts of 0-10% by weight are mentioned below.
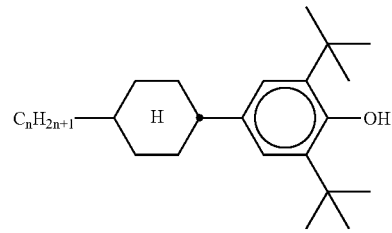
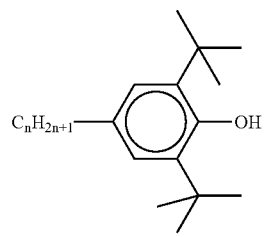
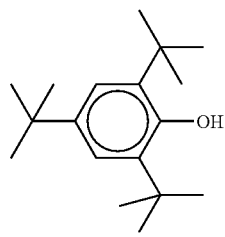
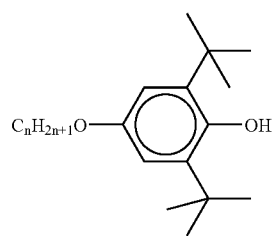
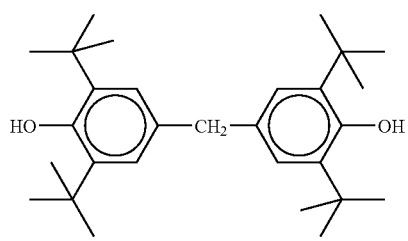
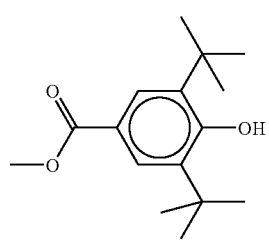

TABLE D-continued
Stabilisers which can be added, for example, to the mixtures according to the invention in amounts of 0-10% by weight are mentioned below.
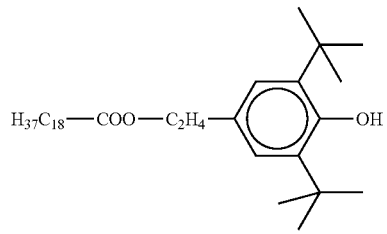
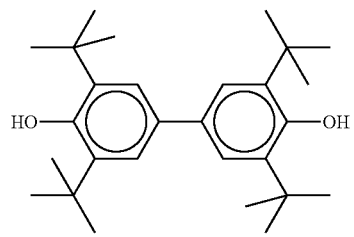
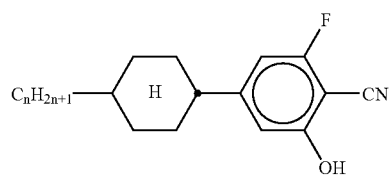
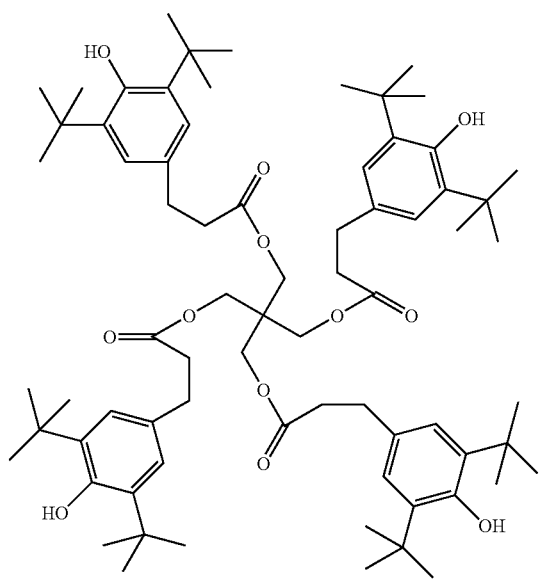
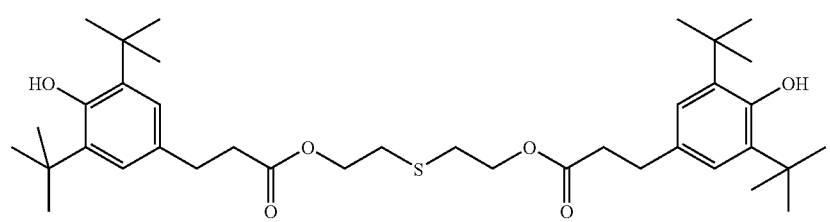

TABLE D-continued
Stabilisers which can be added, for example, to the mixtures according to the invention in amounts of 0-10% by weight are mentioned below.
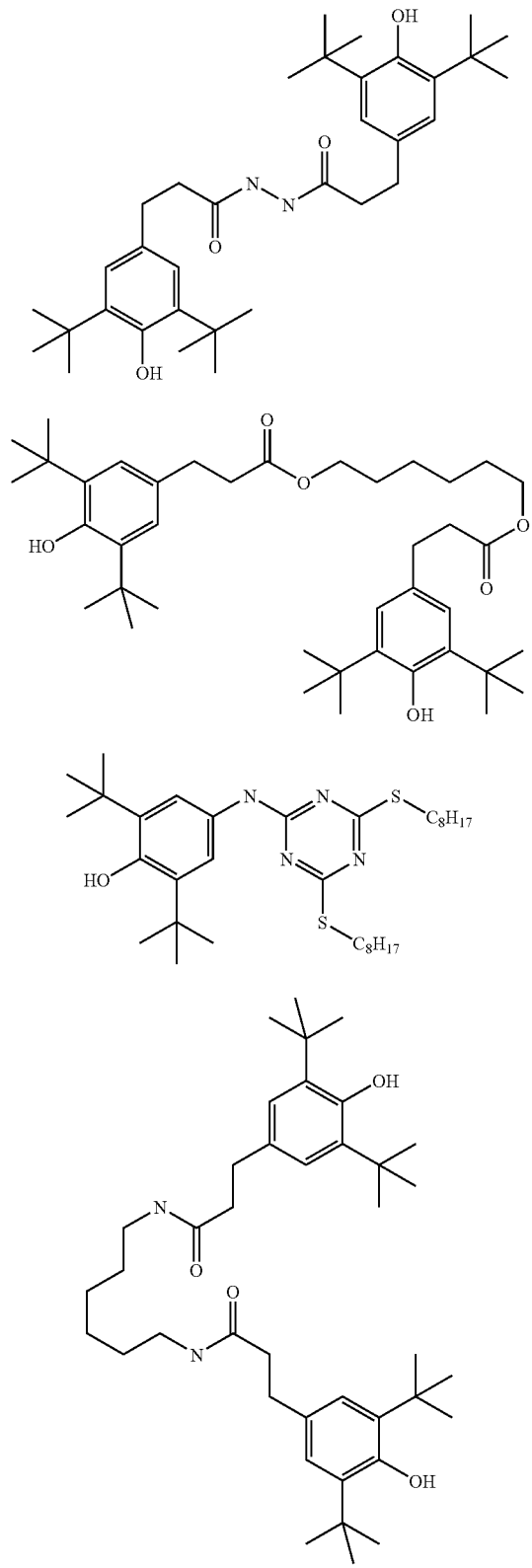

TABLE D-continued
Stabilisers which can be added, for example, to the mixtures according to the invention in amounts of 0-10% by weight are mentioned below.
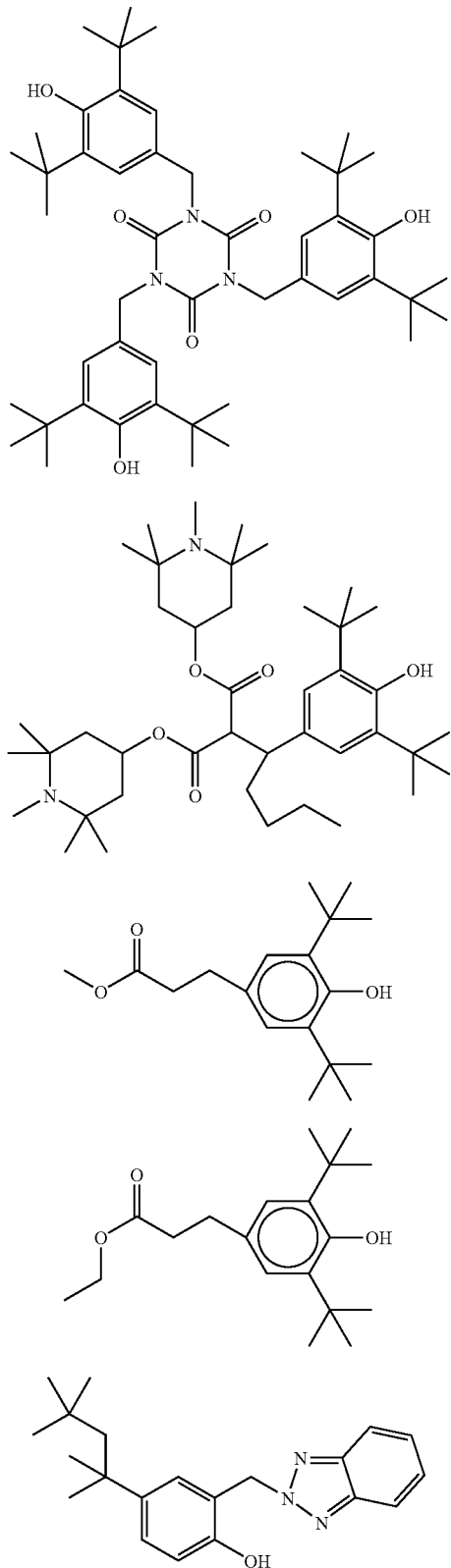

TABLE D-continued
Stabilisers which can be added, for example, to the mixtures according to the invention in amounts of 0-10% by weight are mentioned below.
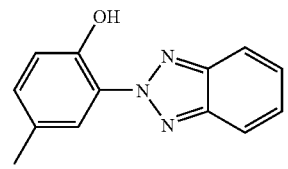
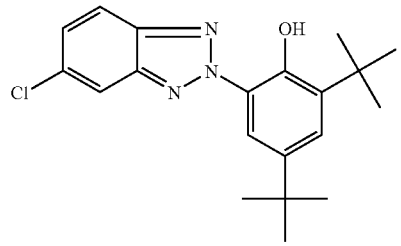
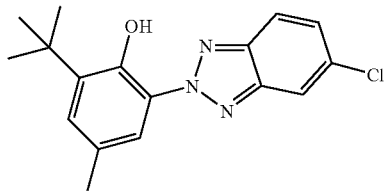
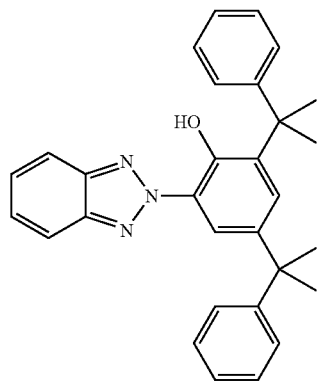
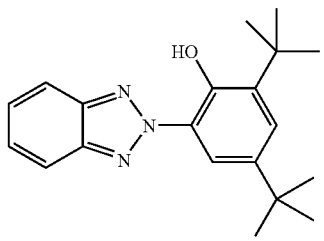
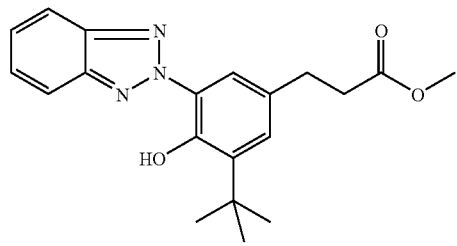

TABLE D-continued
Stabilisers which can be added, for example, to the mixtures according to the invention in amounts of 0-10% by weight are mentioned below.
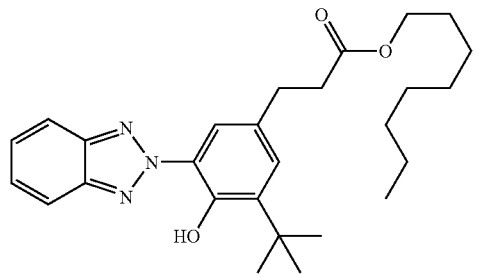
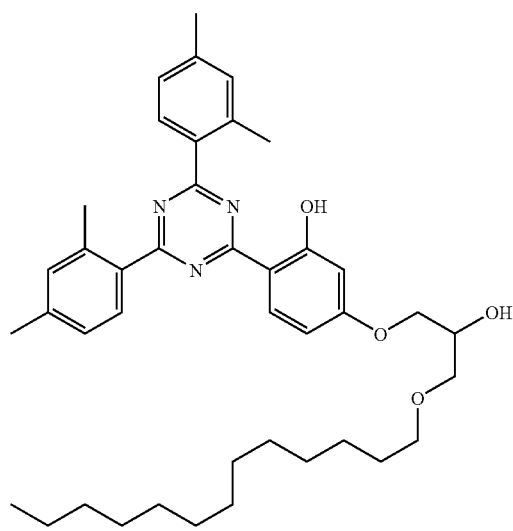
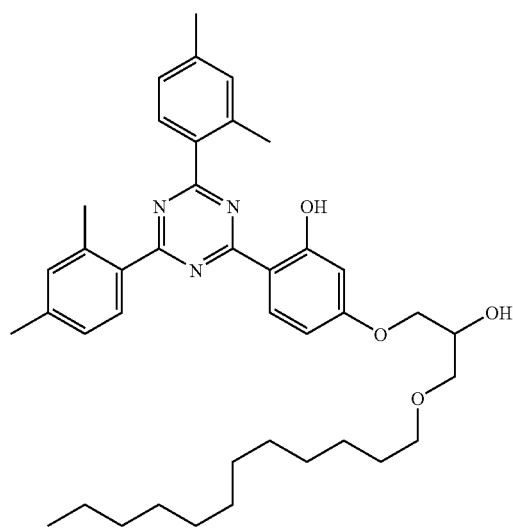

TABLE D-continued

Stabilisers which can be added, for example, to the mixtures according to the invention in amounts of 0-10% by weight are mentioned below.

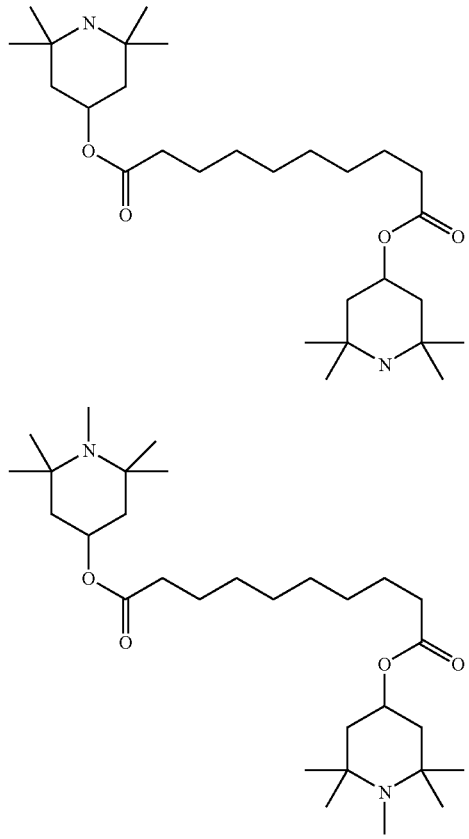

The following examples are intended to explain the invention without restricting it. Above and below, percentages denote percent by weight. All temperatures are indicated in degrees Celsius. m.p. denotes melting point, cl.p. denotes clearing point. Furthermore, C=crystalline state, N=nematic phase, S=smectic phase and I=isotropic phase. The data between these symbols represent the transition temperatures. An denotes optical anisotropy (589 nm, 20° C.). The flow viscosity $v_{20}$ (mm²/sec) and the rotational viscosity $\gamma_1$ (mPa·s) are each determined at 20° C.

"Conventional work-up" means: water is added if desired, the mixture is extracted with methylene chloride, diethyl ether or toluene, the phases are separated, the organic phase is dried and evaporated, and the product is purified by distillation under reduced pressure or crystallisation and/or chromatography.

EXAMPLE 1

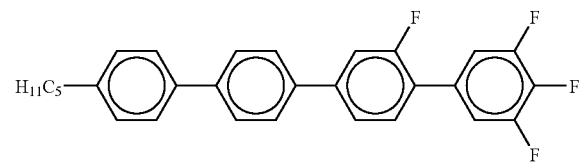

Step 1.1

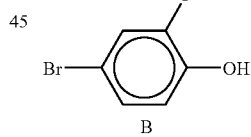
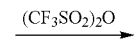
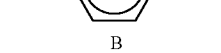

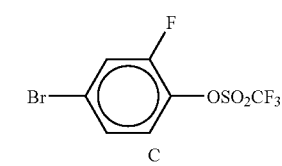

Firstly 51 ml of triethylamine and 650 mg of 4-dimethylaminopyridine and then 262 mmol of trifluoromethanesulfonic anhydride are added to a cold solution (5° C.) of 262 mmol of B in 767 ml of $CH_2Cl_2$. The reaction mixture is allowed to warm to room temperature and is stirred overnight. After addition of 800 ml of n-heptane, the product C is purified by column chromatography.

Step 1.2

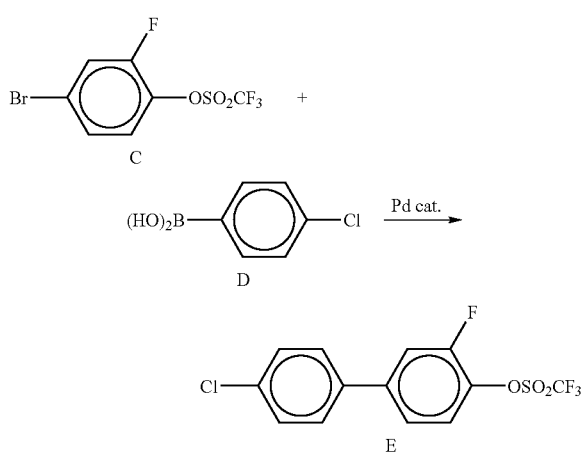

58 mmol of C, 58 mmol of D, 87 mmol of sodium metaborate 8H₂O, 1.1 mmol of bis(triphenylphosphine)PdCl₂ and 1.7 mmol of hydrazine hydroxide are dissolved in 34 ml of water and 66 ml of THF and stirred overnight at 70° C. 100 ml of water are added to the cooled reaction solution. After extraction with methyl tert-butyl ether, the combined organic phases are separated off, washed with water and subjected to conventional work-up.

Step 1.3

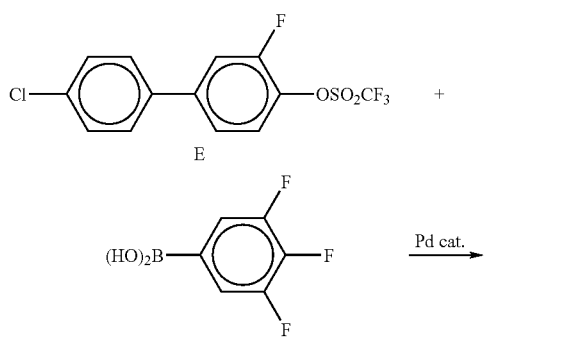

113 mmol of E, 113 mmol of F and 275 mmol of sodium metaborate 8 H₂O, 2.2 mmol of bis(triphenylphosphine)PdCl₂ and 3.4 mmol of hydrazine hydroxide are dissolved in 67 ml of water and 130 ml of THF and heated at 70° C. overnight. 200 ml of water are added to the cooled reaction solution. After extraction with methyl tert-butyl ether, the combined organic phases are washed with water and subjected to conventional work-up.

Step 1.4

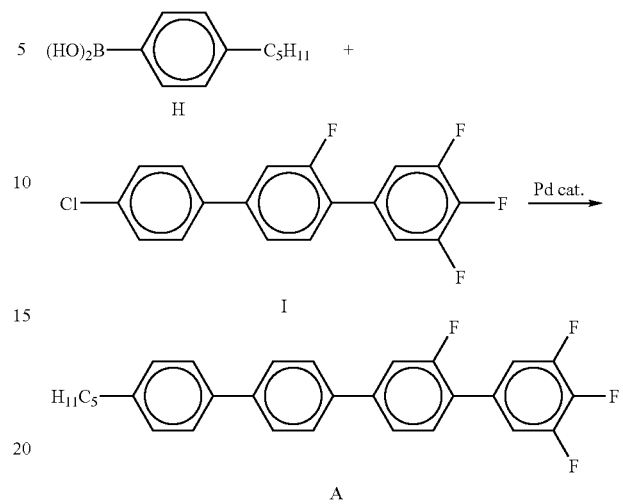

113 mmol of I, 10.8 mmol of H, 152 mmol of caesium fluoride and 0.49 mmol of bis(tricyclohexylphosphine)PdCl₂ are dissolved in 30 ml of 1,4-dioxane and heated at 100° C. overnight. 50 ml of water are added to the cooled reaction solution. After extraction with methyl tert-butyl ether, the combined organic phases are washed with water and subjected to conventional purification.

C 83 $S_E$ 112 $S_A$ 215 N 237.3 I; Δn=0.3060; Δ∈=17.6

The following compounds of the formula

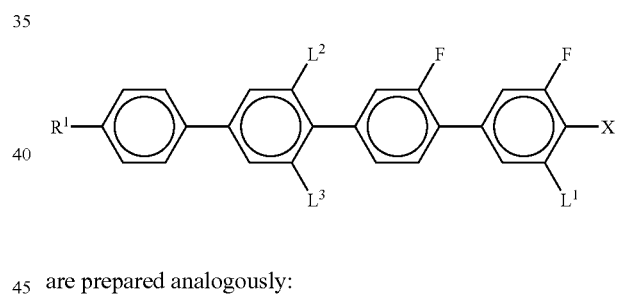

are prepared analogously:

| $R^1$ | X | $L^1$ | $L^2$ | $L^3$ | |
|---|---|---|---|---|---|
| H | F | H | H | H | |
| H | F | F | H | H | |
| H | F | F | F | H | |
| H | F | F | H | F | |
| H | F | F | F | F | |
| CH₃ | F | H | H | H | |
| CH₃ | F | F | H | H | C 178 $S_A$ 215 N 270.6 I |
| CH₃ | F | F | F | H | |
| CH₃ | F | F | H | F | C 176 N 232.3 I |
| CH₃ | F | F | F | F | |
| C₂H₅ | F | H | H | H | |
| C₂H₅ | F | F | H | H | C 149 $S_E$ (139) $S_A$ 209 N 249.5 I Δn = 0.3186; Δ∈ = 20.5 |
| C₂H₅ | F | F | F | H | |
| C₂H₅ | F | F | H | F | C 159 $S_A$ (156) N 208.9 I |
| C₂H₅ | F | F | F | F | |
| C₃H₇ | F | H | H | H | |

-continued

| R¹ | X | L¹ | L² | L³ | |
|---|---|---|---|---|---|
| $C_3H_7$ | F | F | H | H | C 111 $S_E$ 135 $S_A$ 213 N 250.2 I Δn = 0.3270; Δε = 19.9 |
| $C_3H_7$ | F | F | F | H | |
| $C_3H_7$ | F | F | H | F | C 137 $S_A$ 159 N 210.5 I; Δn = 0.2914; Δε = 22.4 |
| $C_3H_7$ | F | F | F | F | |
| $C_4H_9$ | F | H | H | H | |
| $C_4H_9$ | F | F | H | H | C 92 $S_H$ 108 $S_E$ 114 $S_C$ 115 $S_A$ 215 N 239.9 I; Δn = 0.3082; Δε = 19.0 |
| $C_4H_9$ | F | F | F | H | |
| $C_4H_9$ | F | F | H | F | C 112 $S_A$ 166 N 200.1 I; Δn = 0.2910; Δε = 21.1 |
| $C_4H_9$ | F | F | F | F | |
| $C_5H_{11}$ | F | H | H | H | |
| $C_5H_{11}$ | F | F | H | H | |
| $C_5H_{11}$ | F | F | H | F | |
| $C_5H_{11}$ | F | F | F | F | |
| $C_6H_{13}$ | F | H | H | H | |
| $C_6H_{13}$ | F | F | H | H | C 79 $S_E$ 106 $S_A$ 213 N 226.6 I; Δn = 0.2970; Δε = 17.7 |
| $C_6H_{13}$ | F | F | F | H | |
| $C_6H_{13}$ | F | F | H | F | |
| $C_6H_{13}$ | F | F | F | F | |
| $C_7H_{15}$ | F | H | H | H | |
| $C_7H_{15}$ | F | F | H | H | C 68 $S_E$ 103 $S_A$ 214 N 224.1 I; Δn = 0.2938; Δε = 16.4 |
| $C_7H_{15}$ | F | F | F | H | |
| $C_7H_{15}$ | F | F | H | F | |
| $C_7H_{15}$ | F | F | F | F | |
| $CH_2=CH_2$ | F | F | H | H | |
| $CH_2=CH_2$ | F | F | F | H | |
| $CH_2=CH_2$ | F | F | H | F | |
| $CH_2=CH_2$ | F | F | F | F | |
| $CH_3CH=CH$ | F | F | H | H | |
| $CH_3CH=CH$ | F | F | F | H | |
| $CH_3CH=CH$ | F | F | H | F | |
| $CH_3CH=CH$ | F | F | F | F | |
| $CH_2=CHCH_2CH_2$ | F | F | F | H | |
| $CH_2=CHCH_2CH_2$ | F | F | H | F | |
| $CH_2=CHCH_2CH_2$ | F | F | F | F | |
| $CH_3CH=CHCH_2CH_2$ | F | F | F | H | |
| $CH_3CH=CHCH_2CH_2$ | F | F | H | F | |
| $CH_3CH=CHCH_2CH_2$ | F | F | F | F | |
| $CH_3O$ | F | H | H | H | |
| $CH_3O$ | F | F | H | H | |
| $CH_3O$ | F | F | F | H | |
| $CH_3O$ | F | F | H | F | |
| $CH_3O$ | F | F | F | F | |
| $C_2H_5O$ | F | H | H | H | |
| $C_2H_5O$ | F | F | H | H | |
| $C_2H_5O$ | F | F | F | H | |
| $C_2H_5O$ | F | F | H | F | |
| $C_2H_5O$ | F | F | F | F | |
| $C_3H_7O$ | F | H | H | H | |
| $C_3H_7O$ | F | F | H | H | |
| $C_3H_7O$ | F | F | F | H | |
| $C_3H_7O$ | F | F | H | F | |
| $C_3H_7O$ | F | F | F | F | |
| $CH_3OCH_2$ | F | H | H | H | |

-continued

| R¹ | X | L¹ | L² | L³ |
|---|---|---|---|---|
| $CH_3OCH_2$ | F | F | H | H |
| $CH_3OCH_2$ | F | F | F | H |
| $CH_3OCH_2$ | F | F | H | F |
| $CH_3OCH_2$ | F | F | F | F |
| H | Cl | H | H | H |
| H | Cl | F | H | H |
| H | Cl | F | F | H |
| H | Cl | F | H | F |
| H | Cl | F | F | F |
| $CH_3$ | Cl | H | H | H |
| $CH_3$ | Cl | F | H | H |
| $CH_3$ | Cl | F | F | H |
| $CH_3$ | Cl | F | H | F |
| $CH_3$ | Cl | F | F | F |
| $C_2H_5$ | Cl | H | H | H |
| $C_2H_5$ | Cl | F | H | H |
| $C_2H_5$ | Cl | F | F | H |
| $C_2H_5$ | Cl | F | H | F |
| $C_2H_5$ | Cl | F | F | F |
| $C_3H_7$ | Cl | H | H | H |
| $C_3H_7$ | Cl | F | H | H |
| $C_3H_7$ | Cl | F | F | H |
| $C_3H_7$ | Cl | F | H | F |
| $C_3H_7$ | Cl | F | F | F |
| $C_4H_9$ | Cl | H | H | H |
| $C_4H_9$ | Cl | F | H | H |
| $C_4H_9$ | Cl | F | F | H |
| $C_4H_9$ | Cl | F | H | F |
| $C_4H_9$ | Cl | F | F | F |
| $C_5H_{11}$ | Cl | H | H | H |
| $C_5H_{11}$ | Cl | F | H | H |
| $C_5H_{11}$ | Cl | F | F | H |
| $C_5H_{11}$ | Cl | F | H | F |
| $C_5H_{11}$ | Cl | F | F | F |
| $C_6H_{13}$ | Cl | H | H | H |
| $C_6H_{13}$ | Cl | F | H | H |
| $C_6H_{13}$ | Cl | F | F | H |
| $C_6H_{13}$ | Cl | F | H | F |
| $C_6H_{13}$ | Cl | F | F | F |
| $CH_2=CH_2$ | Cl | F | H | H |
| $CH_2=CH_2$ | Cl | F | F | H |
| $CH_2=CH_2$ | Cl | F | H | F |
| $CH_2=CH_2$ | Cl | F | F | F |
| $CH_3CH=CH$ | Cl | H | H | H |
| $CH_3CH=CH$ | Cl | F | H | H |
| $CH_3CH=CH$ | Cl | F | F | H |
| $CH_3CH=CH$ | Cl | F | H | F |
| $CH_3CH=CH$ | Cl | F | F | F |
| $CH_2=CHCH_2CH_2$ | Cl | F | F | H |
| $CH_2=CHCH_2CH_2$ | Cl | F | H | F |
| $CH_2=CHCH_2CH_2$ | Cl | F | F | F |
| $CH_3CH=CHCH_2CH_2$ | Cl | F | F | H |
| $CH_3CH=CHCH_2CH_2$ | Cl | F | H | F |
| $CH_3CH=CHCH_2CH_2$ | Cl | F | F | F |
| $CH_3O$ | Cl | H | H | H |
| $CH_3O$ | Cl | F | H | H |
| $CH_3O$ | Cl | F | F | H |
| $CH_3O$ | Cl | F | H | F |
| $CH_3O$ | Cl | F | F | F |
| $C_2H_5O$ | Cl | H | H | H |
| $C_2H_5O$ | Cl | F | H | H |
| $C_2H_5O$ | Cl | F | F | H |
| $C_2H_5O$ | Cl | F | H | F |
| $C_2H_5O$ | Cl | F | F | F |
| $C_3H_7O$ | Cl | H | H | H |
| $C_3H_7O$ | Cl | F | H | H |
| $C_3H_7O$ | Cl | F | F | H |
| $C_3H_7O$ | Cl | F | H | F |
| $C_3H_7O$ | Cl | F | F | F |
| $CH_3OCH_2$ | Cl | H | H | H |
| $CH_3OCH_2$ | Cl | F | H | H |
| $CH_3OCH_2$ | Cl | F | F | H |
| $CH_3OCH_2$ | Cl | F | H | F |
| $CH_3OCH_2$ | Cl | F | F | F |
| H | CN | H | H | H |
| H | CN | F | H | H |

-continued

| R¹ | X | L¹ | L² | L³ |
|---|---|---|---|---|
| H | CN | F | F | H |
| H | CN | F | H | F |
| H | CN | F | F | F |
| CH₃ | CN | H | H | H |
| CH₃ | CN | F | H | H |
| CH₃ | CN | F | F | H |
| CH₃ | CN | F | H | F |
| CH₃ | CN | F | F | F |
| C₂H₅ | CN | H | H | H |
| C₂H₅ | CN | F | H | H |
| C₂H₅ | CN | F | F | H |
| C₂H₅ | CN | F | H | F |
| C₂H₅ | CN | F | F | F |
| C₃H₇ | CN | H | H | H |
| C₃H₇ | CN | F | H | H |
| C₃H₇ | CN | F | F | H |
| C₃H₇ | CN | F | H | F |
| C₃H₇ | CN | F | F | F |
| C₄H₉ | CN | H | H | H |
| C₄H₉ | CN | F | H | H |
| C₄H₉ | CN | F | F | H |
| C₄H₉ | CN | F | H | F |
| C₄H₉ | CN | F | F | F |
| C₅H₁₁ | CN | H | H | H |
| C₅H₁₁ | CN | F | H | H |
| C₅H₁₁ | CN | F | F | H |
| C₅H₁₁ | CN | F | H | F |
| C₅H₁₁ | CN | F | F | F |
| C₆H₁₃ | CN | H | H | H |
| C₆H₁₃ | CN | F | H | H |
| C₆H₁₃ | CN | F | F | H |
| C₆H₁₃ | CN | F | H | F |
| C₆H₁₃ | CN | F | F | F |
| CH₂=CH₂ | CN | H | H | H |
| CH₂=CH₂ | CN | F | H | H |
| CH₂=CH₂ | CN | F | F | H |
| CH₂=CH₂ | CN | F | H | F |
| CH₂=CH₂ | CN | F | F | F |
| CH₃CH=CH | CN | H | H | H |
| CH₃CH=CH | CN | F | H | H |
| CH₃CH=CH | CN | F | F | H |
| CH₃CH=CH | CN | F | H | F |
| CH₃CH=CH | CN | F | F | F |
| CH₂=CHCH₂CH₂ | CN | F | F | H |
| CH₂=CHCH₂CH₂ | CN | F | H | F |
| CH₂=CHCH₂CH₂ | CN | F | F | F |
| CH₃CH=CHCH₂CH₂ | CN | F | F | H |
| CH₃CH=CHCH₂CH₂ | CN | F | H | F |
| CH₃CH=CHCH₂CH₂ | CN | F | F | F |
| CH₃O | CN | H | H | H |
| CH₃O | CN | F | H | H |
| CH₃O | CN | F | F | H |
| CH₃O | CN | F | H | F |
| CH₃O | CN | F | F | F |
| C₂H₅O | CN | H | H | H |
| C₂H₅O | CN | F | H | H |
| C₂H₅O | CN | F | F | H |
| C₂H₅O | CN | F | H | F |
| C₂H₅O | CN | F | F | F |
| C₃H₇O | CN | H | H | H |
| C₃H₇O | CN | F | H | H |
| C₃H₇O | CN | F | F | H |
| C₃H₇O | CN | F | H | F |
| C₃H₇O | CN | F | F | F |
| CH₃OCH₂ | CN | H | H | H |
| CH₃OCH₂ | CN | F | H | H |
| CH₃OCH₂ | CN | F | F | H |
| CH₃OCH₂ | CN | F | H | F |
| CH₃OCH₂ | CN | F | F | F |
| H | OCF₃ | H | H | H |
| H | OCF₃ | F | H | H |
| H | OCF₃ | F | F | H |
| H | OCF₃ | F | H | F |
| H | OCF₃ | F | F | F |
| CH₃ | OCF₃ | H | H | H |
| CH₃ | OCF₃ | F | H | H |
| CH₃ | OCF₃ | F | F | H |
| CH₃ | OCF₃ | F | H | F |
| CH₃ | OCF₃ | F | F | F |
| C₂H₅ | OCF₃ | H | H | H |
| C₂H₅ | OCF₃ | F | H | H |
| C₂H₅ | OCF₃ | F | F | H |
| C₂H₅ | OCF₃ | F | H | F |
| C₂H₅ | OCF₃ | F | F | F |
| C₃H₇ | OCF₃ | H | H | H |
| C₃H₇ | OCF₃ | F | H | H |
| C₃H₇ | OCF₃ | F | F | H |
| C₃H₇ | OCF₃ | F | H | F |
| C₃H₇ | OCF₃ | F | F | F |
| C₄H₉ | OCF₃ | H | H | H |
| C₄H₉ | OCF₃ | F | H | H |
| C₄H₉ | OCF₃ | F | F | H |
| C₄H₉ | OCF₃ | F | H | F |
| C₄H₉ | OCF₃ | F | F | F |
| C₅H₁₁ | OCF₃ | H | H | H |
| C₅H₁₁ | OCF₃ | F | F | H |
| C₅H₁₁ | OCF₃ | F | H | F |
| C₅H₁₁ | OCF₃ | F | F | F |
| C₆H₁₃ | OCF₃ | H | H | H |
| C₆H₁₃ | OCF₃ | F | H | H |
| C₆H₁₃ | OCF₃ | F | F | H |
| C₆H₁₃ | OCF₃ | F | H | F |
| C₆H₁₃ | OCF₃ | F | F | F |
| CH₂=CH₂ | OCF₃ | H | H | H |
| CH₂=CH₂ | OCF₃ | F | H | H |
| CH₂=CH₂ | OCF₃ | F | F | H |
| CH₂=CH₂ | OCF₃ | F | H | F |
| CH₂=CH₂ | OCF₃ | F | F | F |
| CH₃CH=CH | OCF₃ | H | H | H |
| CH₃CH=CH | OCF₃ | F | H | H |
| CH₃CH=CH | OCF₃ | F | F | H |
| CH₃CH=CH | OCF₃ | F | H | F |
| CH₃CH=CH | OCF₃ | F | F | F |
| CH₂=CHCH₂CH₂ | OCF₃ | F | F | H |
| CH₂=CHCH₂CH₂ | OCF₃ | F | H | F |
| CH₂=CHCH₂CH₂ | OCF₃ | F | F | F |
| CH₃CH=CHCH₂CH₂ | OCF₃ | F | F | H |
| CH₃CH=CHCH₂CH₂ | OCF₃ | F | H | F |
| CH₃CH=CHCH₂CH₂ | OCF₃ | F | F | F |
| CH₃O | OCF₃ | H | H | H |
| CH₃O | OCF₃ | F | H | H |
| CH₃O | OCF₃ | F | F | H |
| CH₃O | OCF₃ | F | H | F |
| CH₃O | OCF₃ | F | F | F |
| C₂H₅O | OCF₃ | H | H | H |
| C₂H₅O | OCF₃ | F | H | H |
| C₂H₅O | OCF₃ | F | F | H |
| C₂H₅O | OCF₃ | F | H | F |
| C₂H₅O | OCF₃ | F | F | F |
| C₃H₇O | OCF₃ | H | H | H |
| C₃H₇O | OCF₃ | F | H | H |
| C₃H₇O | OCF₃ | F | F | H |
| C₃H₇O | OCF₃ | F | H | F |
| C₃H₇O | OCF₃ | F | F | F |
| CH₃OCH₂ | OCF₃ | H | H | H |
| CH₃OCH₂ | OCF₃ | F | H | H |
| CH₃OCH₂ | OCF₃ | F | F | H |
| CH₃OCH₂ | OCF₃ | F | H | F |
| CH₃OCH₂ | OCF₃ | F | F | F |
| H | OCHF₂ | H | H | H |
| H | OCHF₂ | F | H | H |
| H | OCHF₂ | F | F | H |
| H | OCHF₂ | F | H | F |
| H | OCHF₂ | F | F | F |
| CH₃ | OCHF₂ | H | H | H |
| CH₃ | OCHF₂ | F | H | H |
| CH₃ | OCHF₂ | F | F | H |
| CH₃ | OCHF₂ | F | H | F |
| CH₃ | OCHF₂ | F | F | F |
| C₂H₅ | OCHF₂ | H | H | H |
| C₂H₅ | OCHF₂ | F | H | H |
| C₂H₅ | OCHF₂ | F | F | H |
| C₂H₅ | OCHF₂ | F | H | F |

-continued

| R¹ | X | L¹ | L² | L³ |
|---|---|---|---|---|
| C₂H₅ | OCHF₂ | F | F | F |
| C₃H₇ | OCHF₂ | H | H | H |
| C₃H₇ | OCHF₂ | F | H | H |
| C₃H₇ | OCHF₂ | F | F | H |
| C₃H₇ | OCHF₂ | F | H | F |
| C₃H₇ | OCHF₂ | F | F | F |
| C₄H₉ | OCHF₂ | H | H | H |
| C₄H₉ | OCHF₂ | F | H | H |
| C₄H₉ | OCHF₂ | F | F | H |
| C₄H₉ | OCHF₂ | F | H | F |
| C₄H₉ | OCHF₂ | F | F | F |
| C₅H₁₁ | OCHF₂ | H | H | H |
| C₅H₁₁ | OCHF₂ | F | H | H |
| C₅H₁₁ | OCHF₂ | F | F | H |
| C₅H₁₁ | OCHF₂ | F | H | F |
| C₅H₁₁ | OCHF₂ | F | F | F |
| C₆H₁₃ | OCHF₂ | H | H | H |
| C₆H₁₃ | OCHF₂ | F | H | H |
| C₆H₁₃ | OCHF₂ | F | F | H |
| C₆H₁₃ | OCHF₂ | F | H | F |
| C₆H₁₃ | OCHF₂ | F | F | F |
| CH₂=CH₂ | OCHF₂ | H | H | H |
| CH₂=CH₂ | OCHF₂ | F | H | H |
| CH₂=CH₂ | OCHF₂ | F | F | H |
| CH₂=CH₂ | OCHF₂ | F | H | F |
| CH₂=CH₂ | OCHF₂ | F | F | F |
| CH₃CH=CH | OCHF₂ | H | H | H |
| CH₃CH=CH | OCHF₂ | F | H | H |
| CH₃CH=CH | OCHF₂ | F | F | H |
| CH₃CH=CH | OCHF₂ | F | H | F |
| CH₃CH=CH | OCHF₂ | F | F | F |
| CH₂=CHCH₂CH₂ | OCHF₂ | F | F | H |
| CH₂=CHCH₂CH₂ | OCHF₂ | F | H | F |
| CH₂=CHCH₂CH₂ | OCHF₂ | F | F | F |
| CH₃CH=CHCH₂CH₂ | OCHF₂ | F | F | H |
| CH₃CH=CHCH₂CH₂ | OCHF₂ | F | H | F |
| CH₃CH=CHCH₂CH₂ | OCHF₂ | F | F | F |
| CH₃O | OCHF₂ | H | H | H |
| CH₃O | OCHF₂ | F | H | H |
| CH₃O | OCHF₂ | F | F | H |
| CH₃O | OCHF₂ | F | H | F |
| CH₃O | OCHF₂ | F | F | F |
| C₂H₅O | OCHF₂ | H | H | H |
| C₂H₅O | OCHF₂ | F | H | H |
| C₂H₅O | OCHF₂ | F | F | H |
| C₂H₅O | OCHF₂ | F | H | F |
| C₂H₅O | OCHF₂ | F | F | F |
| C₃H₇O | OCHF₂ | H | H | H |
| C₃H₇O | OCHF₂ | F | H | H |
| C₃H₇O | OCHF₂ | F | F | H |
| C₃H₇O | OCHF₂ | F | H | F |
| C₃H₇O | OCHF₂ | F | F | F |
| CH₃OCH₂ | OCHF₂ | H | H | H |
| CH₃OCH₂ | OCHF₂ | F | H | H |
| CH₃OCH₂ | OCHF₂ | F | F | H |
| CH₃OCH₂ | OCHF₂ | F | H | F |
| CH₃OCH₂ | OCHF₂ | F | F | F |
| H | OC₂F₅ | H | H | H |
| H | OC₂F₅ | F | H | H |
| H | OC₂F₅ | F | F | H |
| H | OC₂F₅ | F | H | F |
| H | OC₂F₅ | F | F | F |
| CH₃ | OC₂F₅ | H | H | H |
| CH₃ | OC₂F₅ | F | H | H |
| CH₃ | OC₂F₅ | F | F | H |
| CH₃ | OC₂F₅ | F | H | F |
| CH₃ | OC₂F₅ | F | F | F |
| C₂H₅ | OC₂F₅ | H | H | H |
| C₂H₅ | OC₂F₅ | F | H | H |
| C₂H₅ | OC₂F₅ | F | F | H |
| C₂H₅ | OC₂F₅ | F | H | F |
| C₂H₅ | OC₂F₅ | F | F | F |
| C₃H₇ | OC₂F₅ | H | H | H |
| C₃H₇ | OC₂F₅ | F | H | H |
| C₃H₇ | OC₂F₅ | F | F | H |
| C₃H₇ | OC₂F₅ | F | H | F |
| C₃H₇ | OC₂F₅ | F | F | F |
| C₄H₉ | OC₂F₅ | H | H | H |
| C₄H₉ | OC₂F₅ | F | H | H |
| C₄H₉ | OC₂F₅ | F | F | H |
| C₄H₉ | OC₂F₅ | F | H | F |
| C₄H₉ | OC₂F₅ | F | F | F |
| C₅H₁₁ | OC₂F₅ | H | H | H |
| C₅H₁₁ | OC₂F₅ | F | H | H |
| C₅H₁₁ | OC₂F₅ | F | F | H |
| C₅H₁₁ | OC₂F₅ | F | H | F |
| C₅H₁₁ | OC₂F₅ | F | F | F |
| C₆H₁₃ | OC₂F₅ | H | H | H |
| C₆H₁₃ | OC₂F₅ | F | H | H |
| C₆H₁₃ | OC₂F₅ | F | F | H |
| C₆H₁₃ | OC₂F₅ | F | H | F |
| C₆H₁₃ | OC₂F₅ | F | F | F |
| CH₂=CH₂ | OC₂F₅ | H | H | H |
| CH₂=CH₂ | OC₂F₅ | F | H | H |
| CH₂=CH₂ | OC₂F₅ | F | F | H |
| CH₂=CH₂ | OC₂F₅ | F | H | F |
| CH₂=CH₂ | OC₂F₅ | F | F | F |
| CH₃CH=CH | OC₂F₅ | H | H | H |
| CH₃CH=CH | OC₂F₅ | F | H | H |
| CH₃CH=CH | OC₂F₅ | F | F | H |
| CH₃CH=CH | OC₂F₅ | F | H | F |
| CH₃CH=CH | OC₂F₅ | F | F | F |
| CH₂=CHCH₂CH₂ | OC₂F₅ | F | F | H |
| CH₂=CHCH₂CH₂ | OC₂F₅ | F | H | F |
| CH₂=CHCH₂CH₂ | OC₂F₅ | F | F | F |
| CH₃CH=CHCH₂CH₂ | OC₂F₅ | F | F | H |
| CH₃CH=CHCH₂CH₂ | OC₂F₅ | F | H | F |
| CH₃CH=CHCH₂CH₂ | OC₂F₅ | F | F | F |
| CH₃O | OC₂F₅ | H | H | H |
| CH₃O | OC₂F₅ | F | H | H |
| CH₃O | OC₂F₅ | F | F | H |
| CH₃O | OC₂F₅ | F | H | F |
| CH₃O | OC₂F₅ | F | F | F |
| C₂H₅O | OC₂F₅ | H | H | H |
| C₂H₅O | OC₂F₅ | F | H | H |
| C₂H₅O | OC₂F₅ | F | F | H |
| C₂H₅O | OC₂F₅ | F | H | F |
| C₂H₅O | OC₂F₅ | F | F | F |
| C₃H₇O | OC₂F₅ | H | H | H |
| C₃H₇O | OC₂F₅ | F | H | H |
| C₃H₇O | OC₂F₅ | F | F | H |
| C₃H₇O | OC₂F₅ | F | H | F |
| C₃H₇O | OC₂F₅ | F | F | F |
| CH₃OCH₂ | OC₂F₅ | H | H | H |
| CH₃OCH₂ | OC₂F₅ | F | H | H |
| CH₃OCH₂ | OC₂F₅ | F | F | H |
| CH₃OCH₂ | OC₂F₅ | F | H | F |
| CH₃OCH₂ | OC₂F₅ | F | F | F |
| H | OC₃F₇ | H | H | H |
| H | OC₃F₇ | F | H | H |
| H | OC₃F₇ | F | F | H |
| H | OC₃F₇ | F | H | F |
| H | OC₃F₇ | F | F | F |
| CH₃ | OC₃F₇ | H | H | H |
| CH₃ | OC₃F₇ | F | H | H |
| CH₃ | OC₃F₇ | F | F | H |
| CH₃ | OC₃F₇ | F | H | F |
| CH₃ | OC₃F₇ | F | F | F |
| C₂H₅ | OC₃F₇ | H | H | H |
| C₂H₅ | OC₃F₇ | F | H | H |
| C₂H₅ | OC₃F₇ | F | F | H |
| C₂H₅ | OC₃F₇ | F | H | F |
| C₂H₅ | OC₃F₇ | F | F | F |
| C₃H₇ | OC₃F₇ | H | H | H |
| C₃H₇ | OC₃F₇ | F | H | H |
| C₃H₇ | OC₃F₇ | F | F | H |
| C₃H₇ | OC₃F₇ | F | H | F |
| C₃H₇ | OC₃F₇ | F | F | F |
| C₄H₉ | OC₃F₇ | H | H | H |
| C₄H₉ | OC₃F₇ | F | H | H |
| C₄H₉ | OC₃F₇ | F | F | H |
| C₄H₉ | OC₃F₇ | F | H | F |
| C₄H₉ | OC₃F₇ | F | F | F |
| C₅H₁₁ | OC₃F₇ | H | H | H |

-continued

| R¹ | X | L¹ | L² | L³ |
|---|---|---|---|---|
| C₅H₁₁ | OC₃F₇ | F | H | H |
| C₅H₁₁ | OC₃F₇ | F | F | H |
| C₅H₁₁ | OC₃F₇ | F | H | F |
| C₅H₁₁ | OC₃F₇ | F | F | F |
| C₆H₁₃ | OC₃F₇ | H | H | H |
| C₆H₁₃ | OC₃F₇ | F | H | H |
| C₆H₁₃ | OC₃F₇ | F | F | H |
| C₆H₁₃ | OC₃F₇ | F | H | F |
| C₆H₁₃ | OC₃F₇ | F | F | F |
| CH₂=CH₂ | OC₃F₇ | H | H | H |
| CH₂=CH₂ | OC₃F₇ | F | H | H |
| CH₂=CH₂ | OC₃F₇ | F | F | H |
| CH₂=CH₂ | OC₃F₇ | F | H | F |
| CH₂=CH₂ | OC₃F₇ | F | F | F |
| CH₃CH=CH | OC₃F₇ | H | H | H |
| CH₃CH=CH | OC₃F₇ | F | H | H |
| CH₃CH=CH | OC₃F₇ | F | F | H |
| CH₃CH=CH | OC₃F₇ | F | H | F |
| CH₃CH=CH | OC₃F₇ | F | F | F |
| CH₂=CHCH₂CH₂ | OC₃F₇ | F | F | H |
| CH₂=CHCH₂CH₂ | OC₃F₇ | F | H | F |
| CH₂=CHCH₂CH₂ | OC₃F₇ | F | F | F |
| CH₃CH=CHCH₂CH₂ | OC₃F₇ | F | F | H |
| CH₃CH=CHCH₂CH₂ | OC₃F₇ | F | H | F |
| CH₃CH=CHCH₂CH₂ | OC₃F₇ | F | F | F |
| CH₃O | OC₃F₇ | H | H | H |
| CH₃O | OC₃F₇ | F | H | H |
| CH₃O | OC₃F₇ | F | F | H |
| CH₃O | OC₃F₇ | F | H | F |
| CH₃O | OC₃F₇ | F | F | F |
| C₂H₅O | OC₃F₇ | H | H | H |
| C₂H₅O | OC₃F₇ | F | H | H |
| C₂H₅O | OC₃F₇ | F | F | H |
| C₂H₅O | OC₃F₇ | F | H | F |
| C₂H₅O | OC₃F₇ | F | F | F |
| C₃H₇O | OC₃F₇ | H | H | H |
| C₃H₇O | OC₃F₇ | F | H | H |
| C₃H₇O | OC₃F₇ | F | F | H |
| C₃H₇O | OC₃F₇ | F | H | F |
| C₃H₇O | OC₃F₇ | F | F | F |
| CH₃OCH₂ | OC₃F₇ | H | H | H |
| CH₃OCH₂ | OC₃F₇ | F | H | H |
| CH₃OCH₂ | OC₃F₇ | F | F | H |
| CH₃OCH₂ | OC₃F₇ | F | H | F |
| CH₃OCH₂ | OC₃F₇ | F | F | F |
| H | OCF₂CHFCF₃ | H | H | H |
| H | OCF₂CHFCF₃ | F | H | H |
| H | OCF₂CHFCF₃ | F | F | H |
| H | OCF₂CHFCF₃ | F | H | F |
| H | OCF₂CHFCF₃ | F | F | F |
| CH₃ | OCF₂CHFCF₃ | H | H | H |
| CH₃ | OCF₂CHFCF₃ | F | H | H |
| CH₃ | OCF₂CHFCF₃ | F | F | H |
| CH₃ | OCF₂CHFCF₃ | F | H | F |
| CH₃ | OCF₂CHFCF₃ | F | F | F |
| C₂H₅ | OCF₂CHFCF₃ | H | H | H |
| C₂H₅ | OCF₂CHFCF₃ | F | H | H |
| C₂H₅ | OCF₂CHFCF₃ | F | F | H |
| C₂H₅ | OCF₂CHFCF₃ | F | H | F |
| C₂H₅ | OCF₂CHFCF₃ | F | F | F |
| C₃H₇ | OCF₂CHFCF₃ | H | H | H |
| C₃H₇ | OCF₂CHFCF₃ | F | H | H |
| C₃H₇ | OCF₂CHFCF₃ | F | F | H |
| C₃H₇ | OCF₂CHFCF₃ | F | H | F |
| C₃H₇ | OCF₂CHFCF₃ | F | F | F |
| C₄H₉ | OCF₂CHFCF₃ | H | H | H |
| C₄H₉ | OCF₂CHFCF₃ | F | H | H |
| C₄H₉ | OCF₂CHFCF₃ | F | F | H |
| C₄H₉ | OCF₂CHFCF₃ | F | H | F |
| C₄H₉ | OCF₂CHFCF₃ | F | F | F |
| C₅H₁₁ | OCF₂CHFCF₃ | H | H | H |
| C₅H₁₁ | OCF₂CHFCF₃ | F | H | H |
| C₅H₁₁ | OCF₂CHFCF₃ | F | F | H |
| C₅H₁₁ | OCF₂CHFCF₃ | F | H | F |
| C₅H₁₁ | OCF₂CHFCF₃ | F | F | F |
| C₆H₁₃ | OCF₂CHFCF₃ | H | H | H |
| C₆H₁₃ | OCF₂CHFCF₃ | F | H | H |
| C₆H₁₃ | OCF₂CHFCF₃ | F | F | H |
| C₆H₁₃ | OCF₂CHFCF₃ | F | H | F |
| C₆H₁₃ | OCF₂CHFCF₃ | F | F | F |
| CH₂=CH₂ | OCF₂CHFCF₃ | H | H | H |
| CH₂=CH₂ | OCF₂CHFCF₃ | F | H | H |
| CH₂=CH₂ | OCF₂CHFCF₃ | F | F | H |
| CH₂=CH₂ | OCF₂CHFCF₃ | F | H | F |
| CH₂=CH₂ | OCF₂CHFCF₃ | F | F | F |
| CH₃CH=CH | OCF₂CHFCF₃ | H | H | H |
| CH₃CH=CH | OCF₂CHFCF₃ | F | H | H |
| CH₃CH=CH | OCF₂CHFCF₃ | F | F | H |
| CH₃CH=CH | OCF₂CHFCF₃ | F | H | F |
| CH₃CH=CH | OCF₂CHFCF₃ | F | F | F |
| CH₂=CHCH₂CH₂ | OCF₂CHFCF₃ | F | H | F |
| CH₂=CHCH₂CH₂ | OCF₂CHFCF₃ | F | F | F |
| CH₃CH=CHCH₂CH₂ | OCF₂CHFCF₃ | F | F | H |
| CH₃CH=CHCH₂CH₂ | OCF₂CHFCF₃ | F | H | F |
| CH₃CH=CHCH₂CH₂ | OCF₂CHFCF₃ | F | F | F |
| CH₃O | OCF₂CHFCF₃ | H | H | H |
| CH₃O | OCF₂CHFCF₃ | F | H | H |
| CH₃O | OCF₂CHFCF₃ | F | F | H |
| CH₃O | OCF₂CHFCF₃ | F | H | F |
| CH₃O | OCF₂CHFCF₃ | F | F | F |
| C₂H₅O | OCF₂CHFCF₃ | H | H | H |
| C₂H₅O | OCF₂CHFCF₃ | F | H | H |
| C₂H₅O | OCF₂CHFCF₃ | F | F | H |
| C₂H₅O | OCF₂CHFCF₃ | F | H | F |
| C₂H₅O | OCF₂CHFCF₃ | F | F | F |
| C₃H₇O | OCF₂CHFCF₃ | H | H | H |
| C₃H₇O | OCF₂CHFCF₃ | F | H | H |
| C₃H₇O | OCF₂CHFCF₃ | F | F | H |
| C₃H₇O | OCF₂CHFCF₃ | F | H | F |
| C₃H₇O | OCF₂CHFCF₃ | F | F | F |
| CH₃OCH₂ | OCF₂CHFCF₃ | H | H | H |
| CH₃OCH₂ | OCF₂CHFCF₃ | F | H | H |
| CH₃OCH₂ | OCF₂CHFCF₃ | F | F | H |
| CH₃OCH₂ | OCF₂CHFCF₃ | F | H | F |
| CH₃OCH₂ | OCF₂CHFCF₃ | F | F | F |
| H | NCS | H | H | H |
| H | NCS | F | H | H |
| H | NCS | F | F | H |
| H | NCS | F | H | F |
| H | NCS | F | F | F |
| CH₃ | NCS | H | H | H |
| CH₃ | NCS | F | H | H |
| CH₃ | NCS | F | F | H |
| CH₃ | NCS | F | H | F |
| CH₃ | NCS | F | F | F |
| C₂H₅ | NCS | H | H | H |
| C₂H₅ | NCS | F | H | H |
| C₂H₅ | NCS | F | F | H |
| C₂H₅ | NCS | F | H | F |
| C₂H₅ | NCS | F | F | F |
| C₃H₇ | NCS | H | H | H |
| C₃H₇ | NCS | F | H | H |
| C₃H₇ | NCS | F | F | H |
| C₃H₇ | NCS | F | H | F |
| C₃H₇ | NCS | F | F | F |
| C₄H₉ | NCS | H | H | H |
| C₄H₉ | NCS | F | H | H |
| C₄H₉ | NCS | F | F | H |
| C₄H₉ | NCS | F | H | F |
| C₄H₉ | NCS | F | F | F |
| C₅H₁₁ | NCS | H | H | H |
| C₅H₁₁ | NCS | F | H | H |
| C₅H₁₁ | NCS | F | F | H |
| C₅H₁₁ | NCS | F | H | F |
| C₅H₁₁ | NCS | F | F | F |
| C₆H₁₃ | NCS | H | H | H |
| C₆H₁₃ | NCS | F | H | H |
| C₆H₁₃ | NCS | F | F | H |
| C₆H₁₃ | NCS | F | H | F |
| C₆H₁₃ | NCS | F | F | F |
| CH₂=CH₂ | NCS | H | H | H |
| CH₂=CH₂ | NCS | F | H | H |
| CH₂=CH₂ | NCS | F | F | H |

-continued

| R¹ | X | L¹ | L² | L³ |
|---|---|---|---|---|
| CH₂=CH₂ | NCS | F | H | F |
| CH₂=CH₂ | NCS | F | F | F |
| CH₃CH=CH | NCS | H | H | H |
| CH₃CH=CH | NCS | F | H | H |
| CH₃CH=CH | NCS | F | F | H |
| CH₃CH=CH | NCS | F | H | F |
| CH₃CH=CH | NCS | F | F | F |
| CH₂=CHCH₂CH₂ | NCS | F | H | H |
| CH₂=CHCH₂CH₂ | NCS | F | H | F |
| CH₂=CHCH₂CH₂ | NCS | F | F | F |
| CH₃CH=CHCH₂CH₂ | NCS | F | H | H |
| CH₃CH=CHCH₂CH₂ | NCS | F | H | F |
| CH₃CH=CHCH₂CH₂ | NCS | F | F | F |
| CH₃O | NCS | H | H | H |
| CH₃O | NCS | F | H | H |
| CH₃O | NCS | F | F | H |
| CH₃O | NCS | F | H | F |
| CH₃O | NCS | F | F | F |
| C₂H₅O | NCS | H | H | H |
| C₂H₅O | NCS | F | H | H |
| C₂H₅O | NCS | F | F | H |
| C₂H₅O | NCS | F | H | F |
| C₂H₅O | NCS | F | F | F |
| C₃H₇O | NCS | H | H | H |
| C₃H₇O | NCS | F | H | H |
| C₃H₇O | NCS | F | F | H |
| C₃H₇O | NCS | F | H | F |
| C₃H₇O | NCS | F | F | F |
| CH₃OCH₂ | NCS | H | H | H |
| CH₃OCH₂ | NCS | F | H | H |
| CH₃OCH₂ | NCS | F | F | H |
| CH₃OCH₂ | NCS | F | H | F |
| CH₃OCH₂ | NCS | F | F | F |
| H | SCN | H | H | H |
| H | SCN | F | H | H |
| H | SCN | F | F | H |
| H | SCN | F | H | F |
| H | SCN | F | F | F |
| CH₃ | SCN | H | H | H |
| CH₃ | SCN | F | H | H |
| CH₃ | SCN | F | F | H |
| CH₃ | SCN | F | H | F |
| CH₃ | SCN | F | F | F |
| C₂H₅ | SCN | H | H | H |
| C₂H₅ | SCN | F | H | H |
| C₂H₅ | SCN | F | F | H |
| C₂H₅ | SCN | F | H | F |
| C₂H₅ | SCN | F | F | F |
| C₃H₇ | SCN | H | H | H |
| C₃H₇ | SCN | F | H | H |
| C₃H₇ | SCN | F | F | H |
| C₃H₇ | SCN | F | H | F |
| C₃H₇ | SCN | F | F | F |
| C₄H₉ | SCN | H | H | H |
| C₄H₉ | SCN | F | H | H |
| C₄H₉ | SCN | F | F | H |
| C₄H₉ | SCN | F | H | F |
| C₄H₉ | SCN | F | F | F |
| C₅H₁₁ | SCN | H | H | H |
| C₅H₁₁ | SCN | F | H | H |
| C₅H₁₁ | SCN | F | F | H |
| C₅H₁₁ | SCN | F | H | F |
| C₅H₁₁ | SCN | F | F | F |
| C₆H₁₃ | SCN | H | H | H |
| C₆H₁₃ | SCN | F | H | H |
| C₆H₁₃ | SCN | F | F | H |
| C₆H₁₃ | SCN | F | H | F |
| C₆H₁₃ | SCN | F | F | F |
| CH₂=CH₂ | SCN | H | H | H |
| CH₂=CH₂ | SCN | F | H | H |
| CH₂=CH₂ | SCN | F | F | H |
| CH₂=CH₂ | SCN | F | H | F |
| CH₂=CH₂ | SCN | F | F | F |
| CH₃CH=CH | SCN | H | H | H |
| CH₃CH=CH | SCN | F | H | H |
| CH₃CH=CH | SCN | F | F | H |
| CH₃CH=CH | SCN | F | H | F |
| CH₃CH=CH | SCN | F | F | F |
| CH₂=CHCH₂CH₂ | SCN | F | H | H |
| CH₂=CHCH₂CH₂ | SCN | F | F | H |
| CH₃CH=CHCH₂CH₂ | SCN | F | H | F |
| CH₃CH=CHCH₂CH₂ | SCN | F | F | H |
| CH₃CH=CHCH₂CH₂ | SCN | F | F | F |
| CH₃O | SCN | H | H | H |
| CH₃O | SCN | F | H | H |
| CH₃O | SCN | F | F | H |
| CH₃O | SCN | F | H | F |
| CH₃O | SCN | F | F | F |
| C₂H₅O | SCN | H | H | H |
| C₂H₅O | SCN | F | H | H |
| C₂H₅O | SCN | F | F | H |
| C₂H₅O | SCN | F | H | F |
| C₂H₅O | SCN | F | F | F |
| C₃H₇O | SCN | H | H | H |
| C₃H₇O | SCN | F | H | H |
| C₃H₇O | SCN | F | F | H |
| C₃H₇O | SCN | F | H | F |
| C₃H₇O | SCN | F | F | F |
| CH₃OCH₂ | SCN | H | H | H |
| CH₃OCH₂ | SCN | F | H | H |
| CH₃OCH₂ | SCN | F | F | H |
| CH₃OCH₂ | SCN | F | H | F |
| CH₃OCH₂ | SCN | F | F | F |
| H | SF₅ | H | H | H |
| H | SF₅ | F | H | H |
| H | SF₅ | F | F | H |
| H | SF₅ | F | H | F |
| H | SF₅ | F | F | F |
| CH₃ | SF₅ | H | H | H |
| CH₃ | SF₅ | F | H | H |
| CH₃ | SF₅ | F | F | H |
| CH₃ | SF₅ | F | H | F |
| CH₃ | SF₅ | F | F | F |
| C₂H₅ | SF₅ | H | H | H |
| C₂H₅ | SF₅ | F | H | H |
| C₂H₅ | SF₅ | F | F | H |
| C₂H₅ | SF₅ | F | H | F |
| C₂H₅ | SF₅ | F | F | F |
| C₃H₇ | SF₅ | H | H | H |
| C₃H₇ | SF₅ | F | H | H |
| C₃H₇ | SF₅ | F | F | H |
| C₃H₇ | SF₅ | F | H | F |
| C₃H₇ | SF₅ | F | F | F |
| C₄H₉ | SF₅ | H | H | H |
| C₄H₉ | SF₅ | F | H | H |
| C₄H₉ | SF₅ | F | F | H |
| C₄H₉ | SF₅ | F | H | F |
| C₄H₉ | SF₅ | F | F | F |
| C₅H₁₁ | SF₅ | H | H | H |
| C₅H₁₁ | SF₅ | F | H | H |
| C₅H₁₁ | SF₅ | F | F | H |
| C₅H₁₁ | SF₅ | F | H | F |
| C₅H₁₁ | SF₅ | F | F | F |
| C₆H₁₃ | SF₅ | H | H | H |
| C₆H₁₃ | SF₅ | F | H | H |
| C₆H₁₃ | SF₅ | F | F | H |
| C₆H₁₃ | SF₅ | F | H | F |
| C₆H₁₃ | SF₅ | F | F | F |
| CH₂=CH₂ | SF₅ | H | H | H |
| CH₂=CH₂ | SF₅ | F | H | H |
| CH₂=CH₂ | SF₅ | F | F | H |
| CH₂=CH₂ | SF₅ | F | H | F |
| CH₂=CH₂ | SF₅ | F | F | F |
| CH₃CH=CH | SF₅ | H | H | H |
| CH₃CH=CH | SF₅ | F | H | H |
| CH₃CH=CH | SF₅ | F | F | H |
| CH₃CH=CH | SF₅ | F | H | F |
| CH₃CH=CH | SF₅ | F | F | F |
| CH₂=CHCH₂CH₂ | SF₅ | F | H | F |
| CH₂=CHCH₂CH₂ | SF₅ | F | F | F |
| CH₃CH=CHCH₂CH₂ | SF₅ | F | F | H |
| CH₃CH=CHCH₂CH₂ | SF₅ | F | H | F |

-continued

| R¹ | X | L¹ | L² | L³ |
|---|---|---|---|---|
| CH₃CH=CHCH₂ | SF₅ | F | F | F |
| CH₃O | SF₅ | H | H | H |
| CH₃O | SF₅ | F | H | H |
| CH₃O | SF₅ | F | F | H |
| CH₃O | SF₅ | F | H | F |
| CH₃O | SF₅ | F | F | F |
| C₂H₅O | SF₅ | H | H | H |
| C₂H₅O | SF₅ | F | H | H |
| C₂H₅O | SF₅ | F | F | H |
| C₂H₅O | SF₅ | F | H | F |
| C₂H₅O | SF₅ | F | F | F |
| C₃H₇O | SF₅ | H | H | H |
| C₃H₇O | SF₅ | F | H | H |
| C₃H₇O | SF₅ | F | F | H |
| C₃H₇O | SF₅ | F | H | F |
| C₃H₇O | SF₅ | F | F | F |
| CH₃OCH₂ | SF₅ | H | H | H |
| CH₃OCH₂ | SF₅ | F | H | H |
| CH₃OCH₂ | SF₅ | F | F | H |
| CH₃OCH₂ | SF₅ | F | H | F |
| CH₃OCH₂ | SF₅ | F | F | F |
| H | CF₃ | H | H | H |
| H | CF₃ | F | H | H |
| H | CF₃ | F | F | H |
| H | CF₃ | F | H | F |
| H | CF₃ | F | F | F |
| CH₃ | CF₃ | H | H | H |
| CH₃ | CF₃ | F | H | H |
| CH₃ | CF₃ | F | F | H |
| CH₃ | CF₃ | F | H | F |
| CH₃ | CF₃ | F | F | F |
| C₂H₅ | CF₃ | H | H | H |
| C₂H₅ | CF₃ | F | H | H |
| C₂H₅ | CF₃ | F | F | H |
| C₂H₅ | CF₃ | F | H | F |
| C₂H₅ | CF₃ | F | F | F |
| C₃H₇ | CF₃ | H | H | H |
| C₃H₇ | CF₃ | F | H | H |
| C₃H₇ | CF₃ | F | F | H |
| C₃H₇ | CF₃ | F | H | F |
| C₃H₇ | CF₃ | F | F | F |
| C₄H₉ | CF₃ | H | H | H |
| C₄H₉ | CF₃ | F | H | H |
| C₄H₉ | CF₃ | F | F | H |
| C₄H₉ | CF₃ | F | H | F |
| C₄H₉ | CF₃ | F | F | F |
| C₅H₁₁ | CF₃ | H | H | H |
| C₅H₁₁ | CF₃ | F | H | H |
| C₅H₁₁ | CF₃ | F | F | H |
| C₅H₁₁ | CF₃ | F | H | F |
| C₅H₁₁ | CF₃ | F | F | F |
| C₆H₁₃ | CF₃ | H | H | H |
| C₆H₁₃ | CF₃ | F | H | H |
| C₆H₁₃ | CF₃ | F | F | H |
| C₆H₁₃ | CF₃ | F | H | F |
| C₆H₁₃ | CF₃ | F | F | F |
| CH₂=CH₂ | CF₃ | H | H | H |
| CH₂=CH₂ | CF₃ | F | H | H |
| CH₂=CH₂ | CF₃ | F | F | H |
| CH₂=CH₂ | CF₃ | F | H | F |
| CH₂=CH₂ | CF₃ | F | F | F |
| CH₃CH=CH | CF₃ | H | H | H |
| CH₃CH=CH | CF₃ | F | H | H |
| CH₃CH=CH | CF₃ | F | F | H |
| CH₃CH=CH | CF₃ | F | H | F |
| CH₃CH=CH | CF₃ | F | F | F |
| CH₂=CHCH₂CH₂ | CF₃ | F | F | H |
| CH₂=CHCH₂CH₂ | CF₃ | F | H | F |
| CH₂=CHCH₂CH₂ | CF₃ | F | F | F |
| CH₃CH=CHCH₂CH₂ | CF₃ | F | F | H |
| CH₃CH=CHCH₂CH₂ | CF₃ | F | H | F |
| CH₃CH=CHCH₂CH₂ | CF₃ | F | F | F |
| CH₃O | CF₃ | H | H | H |
| CH₃O | CF₃ | F | H | H |
| CH₃O | CF₃ | F | F | H |
| CH₃O | CF₃ | F | H | F |
| CH₃O | CF₃ | F | F | F |
| C₂H₅O | CF₃ | H | H | H |
| C₂H₅O | CF₃ | F | H | H |
| C₂H₅O | CF₃ | F | F | H |
| C₂H₅O | CF₃ | F | H | F |
| C₂H₅O | CF₃ | F | F | F |
| C₃H₇O | CF₃ | H | H | H |
| C₃H₇O | CF₃ | F | H | H |
| C₃H₇O | CF₃ | F | F | H |
| C₃H₇O | CF₃ | F | H | F |
| C₃H₇O | CF₃ | F | F | F |
| CH₃OCH₂ | CF₃ | H | H | H |
| CH₃OCH₂ | CF₃ | F | H | H |
| CH₃OCH₂ | CF₃ | F | F | H |
| CH₃OCH₂ | CF₃ | F | H | F |
| CH₃OCH₂ | CF₃ | F | F | F |
| H | C₂F₅ | H | H | H |
| H | C₂F₅ | F | H | H |
| H | C₂F₅ | F | F | H |
| H | C₂F₅ | F | H | F |
| H | C₂F₅ | F | F | F |
| CH₃ | C₂F₅ | H | H | H |
| CH₃ | C₂F₅ | F | H | H |
| CH₃ | C₂F₅ | F | F | H |
| CH₃ | C₂F₅ | F | H | F |
| CH₃ | C₂F₅ | F | F | F |
| C₂H₅ | C₂F₅ | H | H | H |
| C₂H₅ | C₂F₅ | F | H | H |
| C₂H₅ | C₂F₅ | F | F | H |
| C₂H₅ | C₂F₅ | F | H | F |
| C₂H₅ | C₂F₅ | F | F | F |
| C₃H₇ | C₂F₅ | H | H | H |
| C₃H₇ | C₂F₅ | F | H | H |
| C₃H₇ | C₂F₅ | F | F | H |
| C₃H₇ | C₂F₅ | F | H | F |
| C₃H₇ | C₂F₅ | F | F | F |
| C₄H₉ | C₂F₅ | H | H | H |
| C₄H₉ | C₂F₅ | F | H | H |
| C₄H₉ | C₂F₅ | F | F | H |
| C₄H₉ | C₂F₅ | F | H | F |
| C₄H₉ | C₂F₅ | F | F | F |
| C₅H₁₁ | C₂F₅ | H | H | H |
| C₅H₁₁ | C₂F₅ | F | H | H |
| C₅H₁₁ | C₂F₅ | F | F | H |
| C₅H₁₁ | C₂F₅ | F | H | F |
| C₅H₁₁ | C₂F₅ | F | F | F |
| C₆H₁₃ | C₂F₅ | H | H | H |
| C₆H₁₃ | C₂F₅ | F | H | H |
| C₆H₁₃ | C₂F₅ | F | F | H |
| C₆H₁₃ | C₂F₅ | F | H | F |
| C₆H₁₃ | C₂F₅ | F | F | F |
| CH₂=CH₂ | C₂F₅ | H | H | H |
| CH₂=CH₂ | C₂F₅ | F | H | H |
| CH₂=CH₂ | C₂F₅ | F | F | H |
| CH₂=CH₂ | C₂F₅ | F | H | F |
| CH₂=CH₂ | C₂F₅ | F | F | F |
| CH₃CH=CH | C₂F₅ | H | H | H |
| CH₃CH=CH | C₂F₅ | F | H | H |
| CH₃CH=CH | C₂F₅ | F | F | H |
| CH₃CH=CH | C₂F₅ | F | H | F |
| CH₃CH=CH | C₂F₅ | F | F | F |
| CH₂=CHCH₂CH₂ | C₂F₅ | F | F | H |
| CH₂=CHCH₂CH₂ | C₂F₅ | F | H | F |
| CH₂=CHCH₂CH₂ | C₂F₅ | F | F | F |
| CH₃CH=CHCH₂CH₂ | C₂F₅ | F | F | H |
| CH₃CH=CHCH₂CH₂ | C₂F₅ | F | H | F |
| CH₃CH=CHCH₂CH₂ | C₂F₅ | F | F | F |
| CH₃O | C₂F₅ | H | H | H |
| CH₃O | C₂F₅ | F | H | H |
| CH₃O | C₂F₅ | F | F | H |
| CH₃O | C₂F₅ | F | H | F |
| CH₃O | C₂F₅ | F | F | F |
| C₂H₅O | C₂F₅ | H | H | H |
| C₂H₅O | C₂F₅ | F | H | H |
| C₂H₅O | C₂F₅ | F | F | H |
| C₂H₅O | C₂F₅ | F | H | F |
| C₂H₅O | C₂F₅ | F | F | F |
| C₃H₇O | C₂F₅ | H | H | H |

| R¹ | X | L¹ | L² | L³ |
|---|---|---|---|---|
| C₃H₇O | C₂F₅ | F | H | H |
| C₃H₇O | C₂F₅ | F | F | H |
| C₃H₇O | C₂F₅ | F | H | F |
| C₃H₇O | C₂F₅ | F | F | F |
| CH₃OCH₂ | C₂F₅ | H | H | H |
| CH₃OCH₂ | C₂F₅ | F | H | H |
| CH₃OCH₂ | C₂F₅ | F | F | H |
| CH₃OCH₂ | C₂F₅ | F | H | F |
| CH₃OCH₂ | C₂F₅ | F | F | F |

EXAMPLE 2

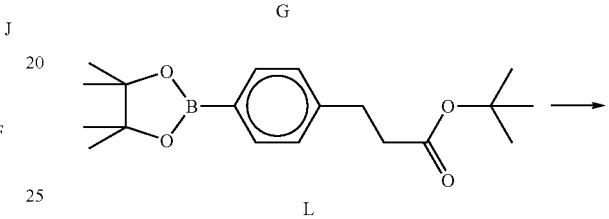

J

Step 2.1

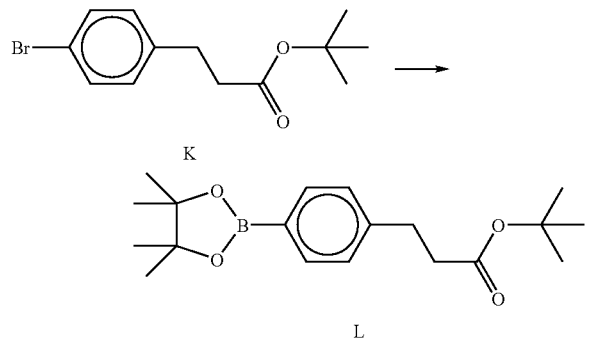

141 mmol of K, 4.2 mmol of PdCl₂-dppf (dppf diphenylphosphinoferrocene), 423 mmol of potassium acetate and 155 mmol of bis(pinacolato)diboron dissolved in 244 ml of 1,4-dioxane are stirred at 100° C. for 16 h. Water is added to the reaction mixture, which is extracted with methyl tert-butyl ether. The combined organic phases are washed with water, dried over sodium sulfate, filtered and evaporated in a rotary evaporator. The residue is eluted over 2 l of silica gel with heptane/methyl tert-butyl ether (3:1).

Step 2.2

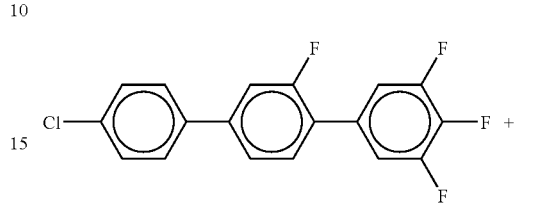

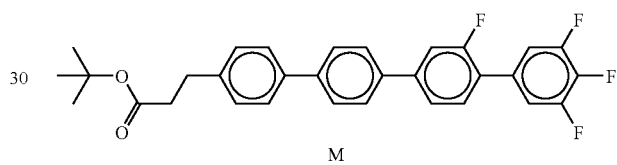

71 mmol of G, 78 mmol of L, 141 mmol of caesium fluoride, 3.55 mmol of bis(tricyclohexylphosphine)PdCl₂ and 396 ml of 1,4-dioxane are stirred at 100° C. overnight in a nitrogen atmosphere. The reaction mixture is allowed to cool, water is added, and the mixture is extracted with dichloromethane. The combined organic phases are washed with water, dried over sodium sulfate, filtered and evaporated in a rotary evaporator. The residue is eluted over 1.5 l of silica gel with hot toluene.

Step 2.3

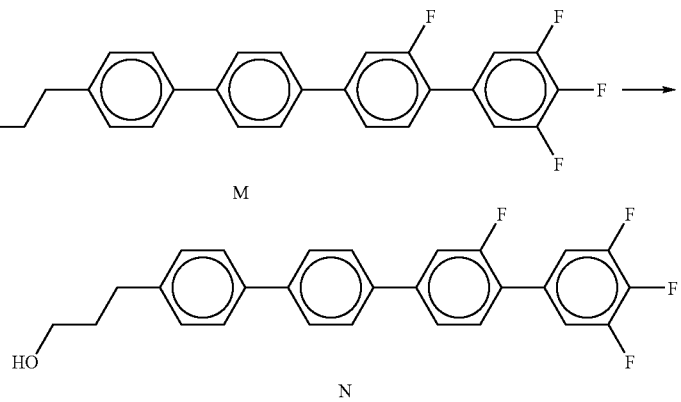

47.4 mmol of diisobutylaluminium hydride (DiBALH solution in toluene) are added at 0° C. to 23.7 mmol of M in 240 ml of toluene, and the mixture is stirred at room temperature overnight. The reaction mixture is poured onto ice and warmed to room temperature with stirring. During the warming, dilute hydrochloric acid (2N) is added. After extraction with methyl tert-butyl ether, the combined organic phases are washed with water, dried over sodium sulfate, filtered and evaporated in a rotary evaporator. The crude product is eluted over 500 ml of silica gel. Finally, the product is chromatographed with dichloromethane/methyl tert-butyl ether (1:1).

Step 2.4

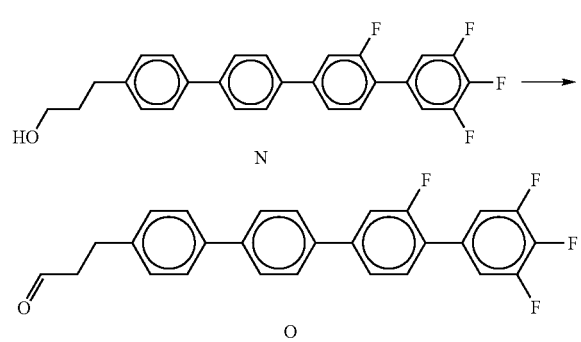

1412 µmol of KBr in 2.8 ml of demineralised water are initially introduced, and 14 mmol of N in 26 ml of dichloromethane are added. After addition of 141 µmol of TEMPO (2,2,6,6-tetramethylpiperidin-1-oxyl), the reaction mixture is cooled to 0° C. At this temperature, 17.7 mmol of sodium hypochlorite solution (6-14% of active chlorine) which is adjusted in advance to about pH=8.5 using sodium hydrogencarbonate solution are added. After stirring for 0.5 h, sodium hypochlorite solution is again added until starting material is no longer present in the reaction solution. The reaction mixture is diluted with water and extracted with dichloromethane. The combined organic phases are washed with water, dried over sodium sulfate, filtered and evaporated in a rotary evaporator.

Step 2.5

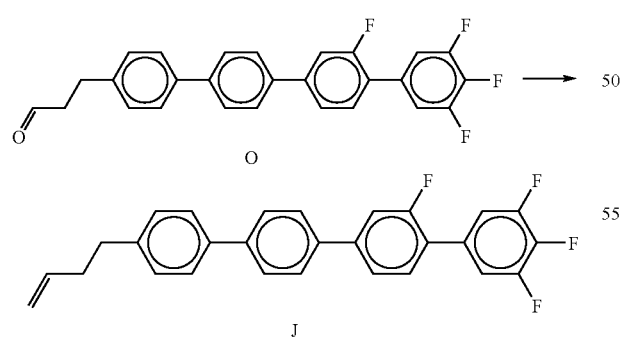

6.3 mmol of potassium tert-butoxide in 13 ml of THF are added at 0° C. to 5.3 mmol of O, 6.3 mmol of methyltriphenylphosphonium bromide in 12 ml of THF. The mixture is left to stir overnight at room temperature. The reaction mixture is acidified and extracted with dichloromethane. The combined organic phases are washed with water, dried over sodium sulfate, filtered and evaporated in a rotary evaporator. The product is subsequently subjected to conventional work-up.

C 106 $S_E$ 124 $S_C$ 152 $S_A$ 176 N 251.6 I

The following compounds of the formula

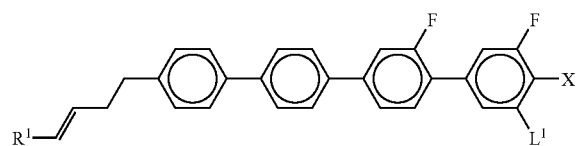

are prepared analogously:

| X | $R^1$ | $L^1$ | |
|---|---|---|---|
| F | H | H | |
| Cl | H | H | |
| Cl | H | F | |
| CN | H | H | |
| CN | H | F | |
| $OCF_3$ | H | H | |
| $OCF_3$ | H | F | |
| $OCHF_2$ | H | H | |
| $OCHF_2$ | H | F | |
| $OC_2F_5$ | H | H | |
| $OC_2F_5$ | H | F | |
| $OC_3F_7$ | H | H | |
| $OC_3F_7$ | H | F | |
| $OCF_2CHFCF_3$ | H | H | |
| $OCF_2CHFCF_3$ | H | F | |
| NCS | H | H | |
| NCS | H | F | |
| SCN | H | H | |
| SCN | H | F | |
| $SF_5$ | H | H | |
| $SF_5$ | H | F | |
| $CF_3$ | H | H | |
| $CF_3$ | H | F | |
| $C_2F_5$ | H | H | |
| $C_2F_5$ | H | F | |
| $OCH_2F$ | H | H | |
| $OCH_2F$ | H | F | |
| F | $CH_3$ | H | |
| F | $CH_3$ | F | $S_E$ 165 $S_A$ 214 N 263.3 I |
| Cl | $CH_3$ | H | |
| Cl | $CH_3$ | F | |
| CN | $CH_3$ | H | |
| CN | $CH_3$ | F | |
| $OCF_3$ | $CH_3$ | H | |
| $OCF_3$ | $CH_3$ | F | |
| $OCHF_2$ | $CH_3$ | H | |
| $OCHF_2$ | $CH_3$ | F | |
| $OC_2F_5$ | $CH_3$ | H | |
| $OC_2F_5$ | $CH_3$ | F | |
| $OC_3F_7$ | $CH_3$ | H | |
| $OC_3F_7$ | $CH_3$ | F | |
| $OCF_2CHFCF_3$ | $CH_3$ | H | |
| $OCF_2CHFCF_3$ | $CH_3$ | F | |
| NCS | $CH_3$ | H | |
| NCS | $CH_3$ | F | |
| SCN | $CH_3$ | H | |
| SCN | $CH_3$ | F | |
| $SF_5$ | $CH_3$ | H | |
| $SF_5$ | $CH_3$ | F | |
| $CF_3$ | $CH_3$ | H | |
| $CF_3$ | $CH_3$ | F | |
| $C_2F_5$ | $CH_3$ | H | |
| $C_2F_5$ | $CH_3$ | F | |
| $OCH_2F$ | $CH_3$ | H | |
| $OCH_2F$ | $CH_3$ | F | |

Mixture Examples

Example M1

| | | | |
|---|---|---|---|
| PGP-2-3 | 15.00% | Clearing point [° C.]: | 88.0 |
| PGP-2-4 | 15.00% | Δn [589 nm, 20° C.]: | 0.2023 |
| PGP-3-2 | 9.00% | Δε [1 kHz, 20° C.]: | 5.0 |
| PCH-301 | 19.00% | $K_1$ [pN, 20° C.]: | 13.0 |
| GGP-2-F | 9.00% | $\gamma_1$ [mPa·s, 20° C.]: | 154 |
| GGP-3-F | 11.00% | $V_0$ [V]: | 1.70 |
| CGG-3-F | 16.00% | | |
| PPGU-3-F | 6.00% | | |

Example M2

| | |
|---|---|
| PGP-2-3 | 14.00% |
| PGP-2-4 | 14.00% |
| PGP-3-2 | 10.00% |
| PCH-301 | 21.00% |
| GGP-2-F | 9.00% |
| GGP-3-F | 9.00% |
| CGG-3-F | 15.00% |
| PPGU-3-F | 4.00% |
| PPGU-5-F | 4.00% |

The invention claimed is:

1. Liquid-crystalline medium based on a mixture of polar compounds, comprising

A) one or more compounds of formula I

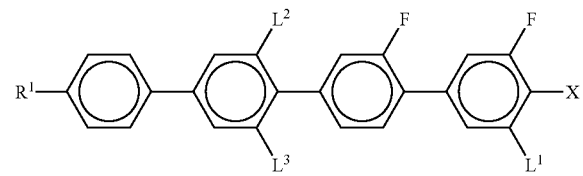

in which
- $R^1$ denotes a halogenated or unsubstituted alkyl or alkoxy radical having 1 to 15 C atoms, in which optionally one or more $CH_2$ groups are each, independently of one another, replaced by -◊-, -◊◊-, —CH=CH—, —O—, —$CF_2$O—, —O$CF_2$—, —CO—O— or —O—CO— in such a way that O atoms are not linked directly to one another,
- X denotes F, Cl, CN, $SF_5$, SCN, NCS, a halogenated alkyl radical, a halogenated alkenyl radical, a halogenated alkoxy radical or a halogenated alkenyloxy radical having up to 6 C atoms,
- $L^1$ is F, and
- $L^2$ and $L^3$ are H, and B) one or more compounds of formula I*

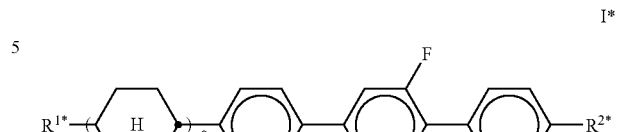

in which
- $R^{1*}$ and $R^{2*}$ each, independently of one another, denote alkyl, alkoxy, oxaalkyl, fluoroalkyl, alkenyloxy or alkenyl, each having up to 9 C atoms, and
- r* denotes 0 or 1.

2. Liquid-crystalline medium according to claim 1, which comprises one or more compounds of formula I-1, I-2, I-3, I-4, I-5, I-6, I-7, I-8, I-9 or I-10

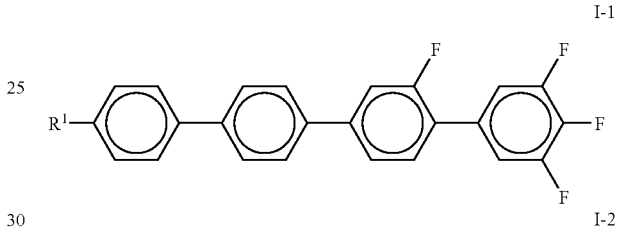

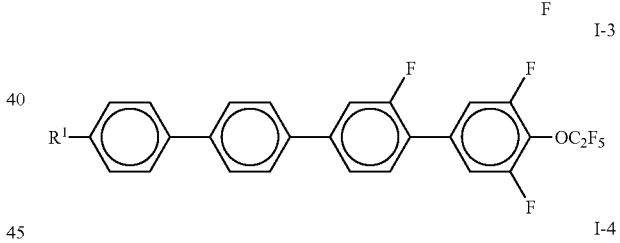

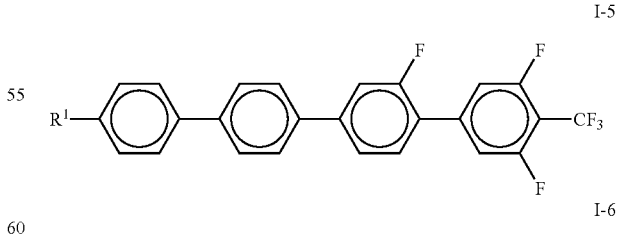

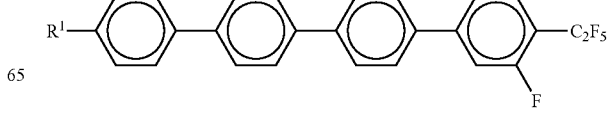

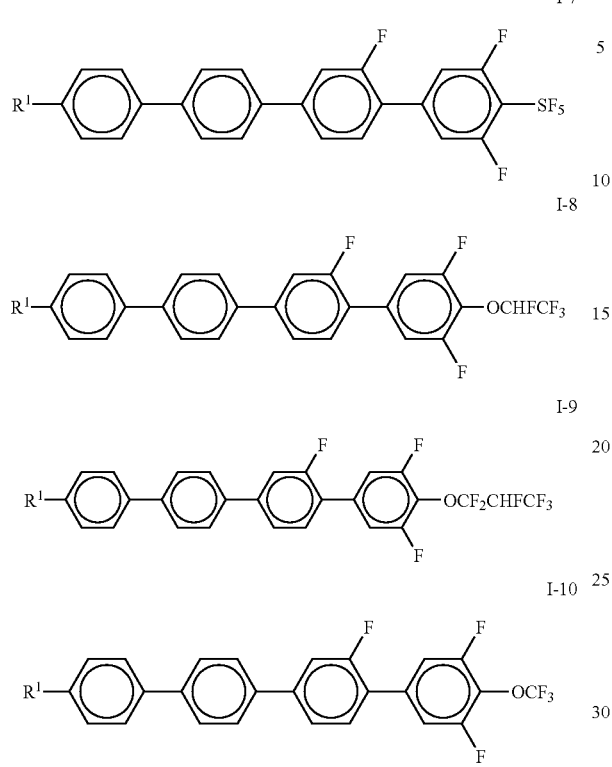

in which R¹ has the meaning indicated in claim 1.

3. Liquid-crystalline medium according to claim 1, wherein R¹ denotes alkyl or alkenyl.

4. Liquid-crystalline medium according to claim 1, which comprises one or more compounds of formula I*-1, I*-2, I*-3, I*-4, I*-5, I*-6, I*-7 or I*-8

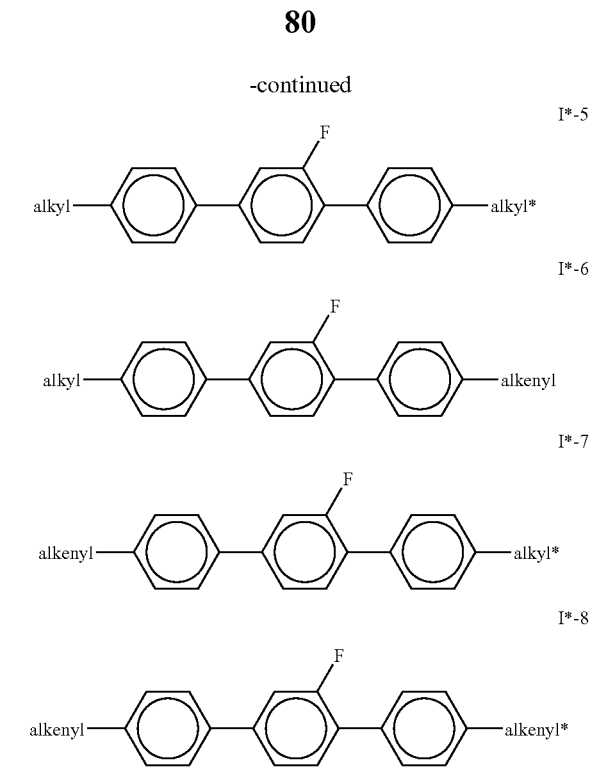

in which alkyl and alkyl* each, independently of one another, denote straight-chain alkyl having 1-6 C atoms, and alkenyl and alkenyl* each, independently of one another, denote straight-chain alkenyl having 2-6 C atoms.

5. Liquid-crystalline medium according to claim 1, which further comprises one or more compounds of formula XIII, XIV, XV, XVI, XVII, XVIII or XIX

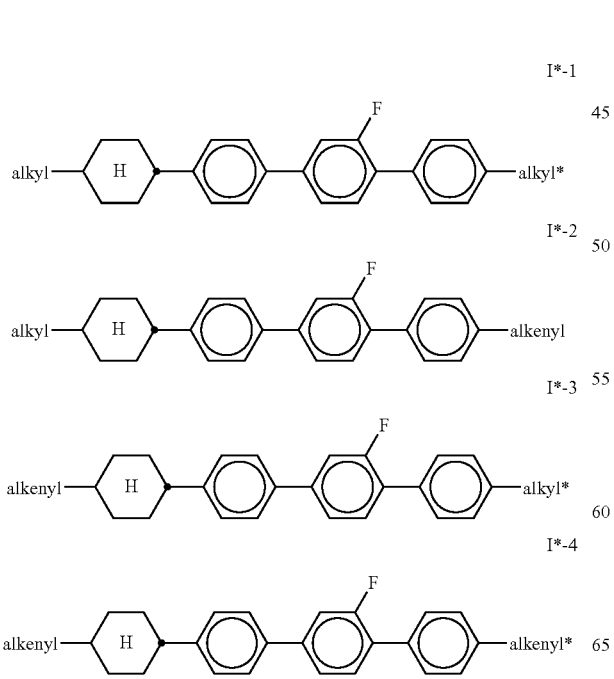

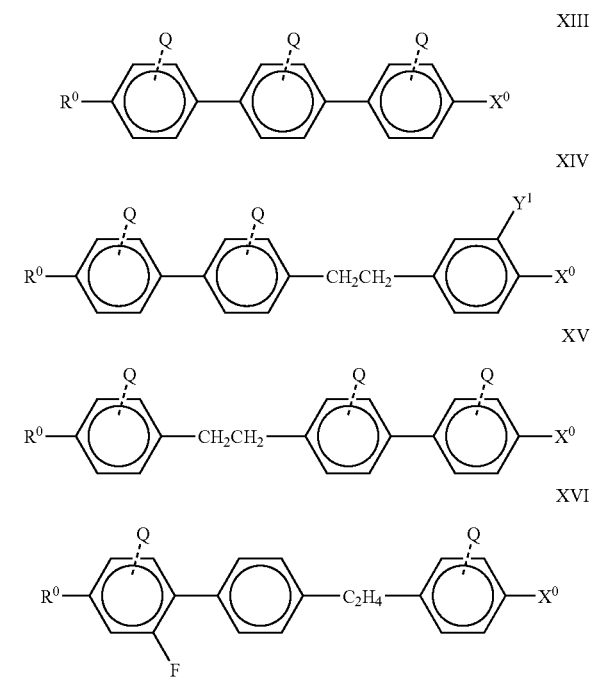

-continued

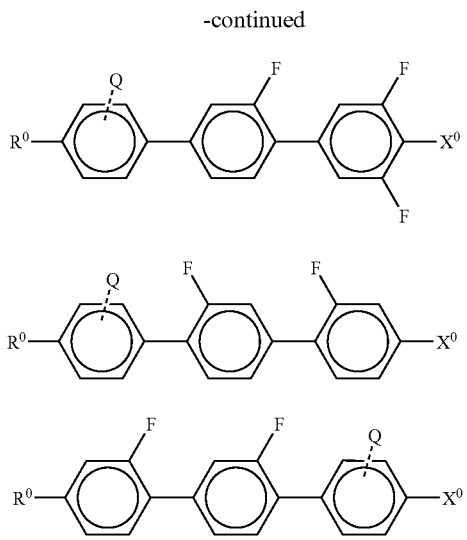

in which
R⁰ denotes alkyl, alkoxy, oxaalkyl, fluoroalkyl or alkenyl, each having up to 9 C atoms,
Y¹ is H or F.
X⁰ denotes F, CN, halogenated alkyl, halogenated alkenyl, halogenated oxaalkyl, halogenated alkenyloxy or halogenated alkoxy having up to 6 C atoms, and
Q is zero, one or more substituents Cl or F.

6. Liquid-crystalline medium according to claim 5, wherein the proportion of compounds of formulae XIII to XIX together in the mixture as a whole is at least 0.05-30% by weight.

7. Liquid-crystalline medium according to claim 1, which further comprises one or more compounds of formula II, III, IV, V or VI

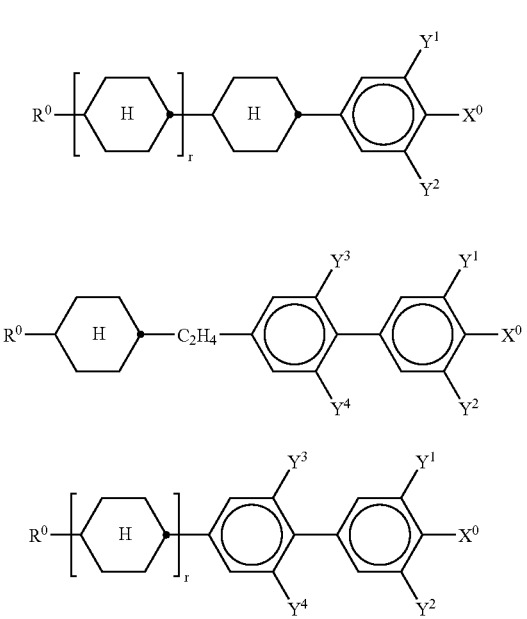

-continued

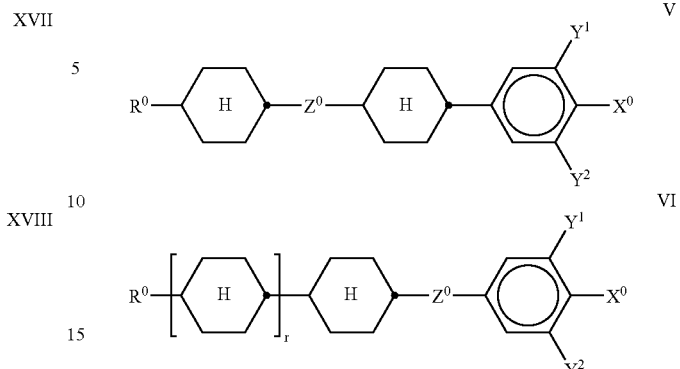

in which
R⁰ denotes alkyl, alkoxy, oxaalkyl, fluoroalkyl or alkenyl, each having up to 9 C atoms,
X⁰ denotes F, Cl, halogenated alkyl, halogenated alkenyl, halogenated oxaalkyl, halogenated alkenyloxy or halogenated alkoxy having up to 6 C atoms,
Z⁰ denotes —C₂F₄—, —CF=CF, —CH=CH—, —C₂H₄—, —(CH₂)₄—, —OCH₂—, —CH₂O—, —CF₂O— or —OCF₂—,
Y¹ to Y⁴ each, independently of one another, denote H or F, and
r denotes 0 or 1.

8. Liquid-crystalline medium according to claim 1, wherein the proportion of compounds of formula I in the mixture as a whole is 0.01 to 30.0% by weight.

9. Liquid-crystalline medium according to claim 1, wherein the proportion of compounds of the formulae I and I* in the mixture as a whole is at least 5% by weight.

10. Electro-optical liquid-crystal display containing a liquid-crystalline medium according to claim 1.

11. A compound of formula I

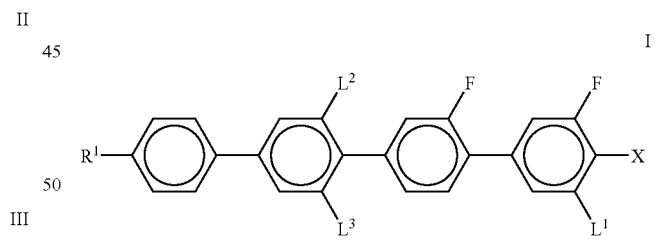

in which
R¹ denotes a halogenated or unsubstituted alkyl or alkoxy radical having 1 to 15 C atoms, in which optionally one or more CH₂ groups are each, independently of one another, replaced by —CH≡CH—, —O—, —CF₂O—, —OCF₂—, —CO—O— or —O—CO— in such a way that O atoms are not linked directly to one another,
X denotes F, Cl, CN, SF₅, SCN, NCS, a halogenated alkyl radical, a halogenated alkenyl radical, a halogenated alkoxy radical or a halogenated alkenyloxy radical having up to 6 C atoms,
L¹ is F, and
L² and L³ are H.

12. A compound of formula I-1, I-2, I-3, I-4, I-5, I-6, I-7, I-8, I-9 or I-10

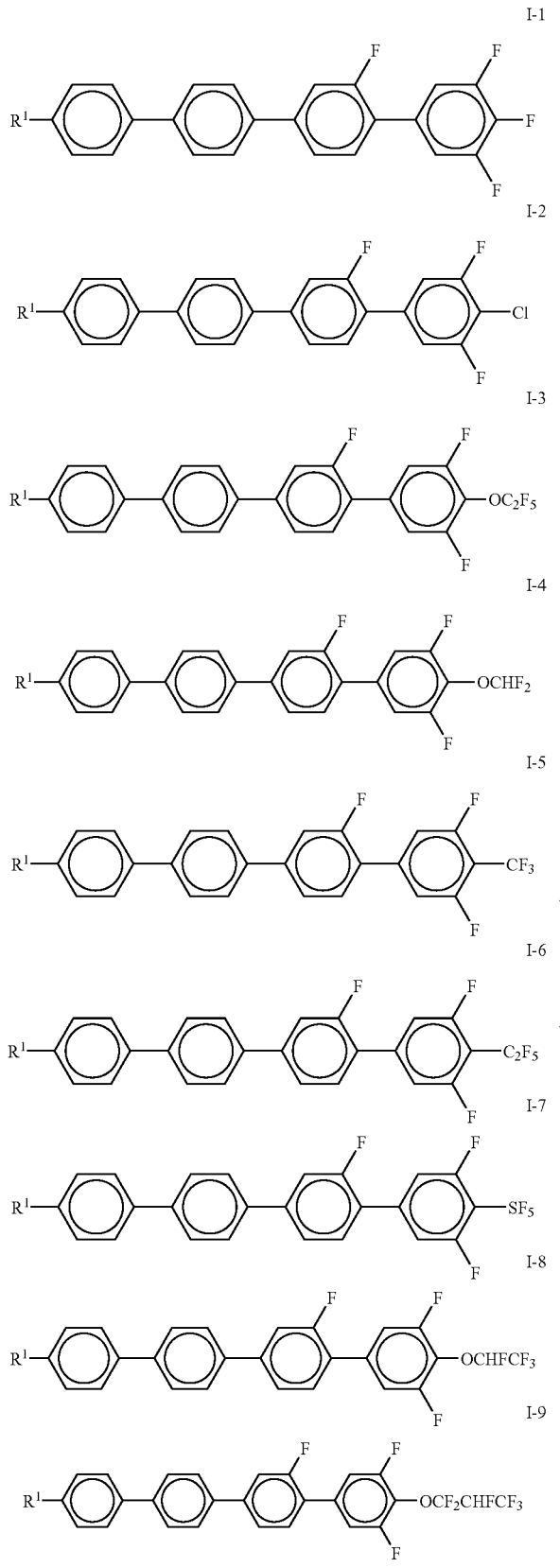

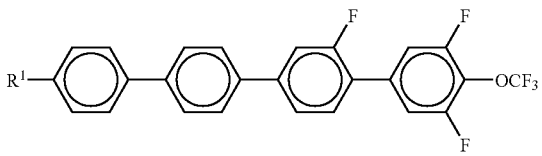

in which
R¹ denotes a halogenated or unsubstituted alkyl or alkoxy radical having 1 to 15 C atoms, in which optionally one or more $CH_2$ groups are each, independently of one another, replaced by —CH≡CH—, —CH═CH—, —O—, —CF$_2$O—, —OCF$_2$—, —CO—O— or —O—CO— in such a way that O atoms are not linked directly to one another.

13. Liquid-crystalline medium according to claim 1, which further comprises one or more compounds of formula XIII, XIV, XV, XVI, XVII, XVIII or XIX

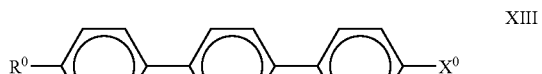

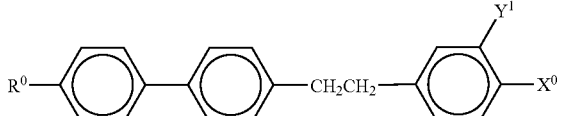

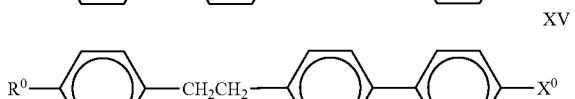

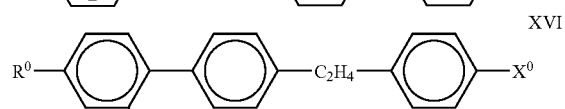

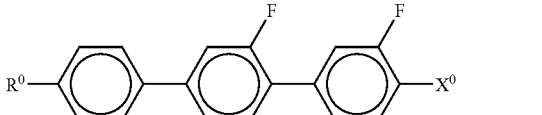

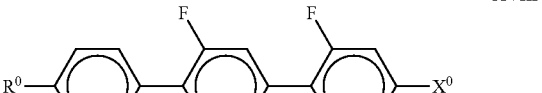

in which
R⁰ denotes alkyl, alkoxy, oxaalkyl, fluoroalkyl or alkenyl, each having up to 9 C atoms,
Y¹ is H or F, and X⁰ denotes F, CN, halogenated alkyl, halogenated alkenyl, halogenated oxaalkyl, halogenated alkenyloxy or halogenated alkoxy having up to 6 C atoms.

14. Liquid-crystalline medium according to claim 2, which comprises one or more compounds of formula I-1, I-4, I-7 or I-10.

15. Liquid-crystalline medium according to claim 2, which comprises one or more compounds of formula I-1 or I-10.

16. Liquid-crystalline medium according to claim 4, which comprises one or more compounds of formula I*-5, I*-6 or I*-7.

17. Liquid-crystalline medium according to claim 4, which comprises one or more compounds of formula I*-5.

18. Liquid-crystalline medium according to claim 2, which comprises
one or more compounds of formula I-1 or I-10, and
one or more compounds of formula I*-5

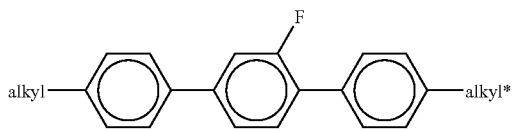

I*-5 in which
alkyl and alkyl* each, independently of one another, denote straight-chain alkyl having 1-6 C atoms.

19. Liquid-crystalline medium based on a mixture of polar compounds, comprising
one or more compounds according to claim 11, and
one or more compounds of formula I*

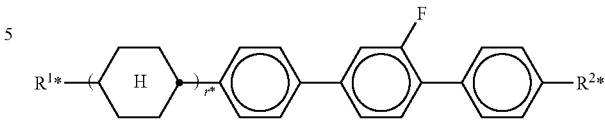

I* in which
$R^{1*}$ and $R^{2*}$ each, independently of one another, denote alkyl, alkoxy, oxaalkyl, fluoroalkyl, alkenyloxy or alkenyl, each having up to 9 C atoms, and
r* denotes 0 or 1.

20. Liquid-crystalline medium based on a mixture of polar compounds, comprising
one or more compounds according to claim 12, and
one or more compounds of formula I*

I* in which
$R^{1*}$ and $R^{2*}$ each, independently of one another, denote alkyl, alkoxy, oxaalkyl, fluoroalkyl, alkenyloxy or alkenyl, each having up to 9 C atoms, and
r* denotes 0 or 1.

* * * * *

UNITED STATES PATENT AND TRADEMARK OFFICE
CERTIFICATE OF CORRECTION

PATENT NO. : 7,732,021 B2
APPLICATION NO. : 11/629631
DATED : June 8, 2010
INVENTOR(S) : Atsutaka Manabe It is certified that error appears in the above-identified patent and that said Letters Patent is hereby corrected as shown below:

Column 77, Line 56 reads: "another, replaced by "  ,  , -CH=CH-"

Should read: -- another, replaced by  ,  , -C≡C-, -CH=CH-, --

Signed and Sealed this

Twenty-eighth Day of September, 2010

David J. Kappos
*Director of the United States Patent and Trademark Office*